United States Patent
Cho et al.

(10) Patent No.: US 10,321,272 B2
(45) Date of Patent: Jun. 11, 2019

(54) METHOD FOR PROVIDING ACTIVITY INFORMATION OF OTHER RELATED TO ACTIVITY PATTERN OF USER AND ELECTRONIC DEVICE THEREOF

(71) Applicant: Samsung Electronics Co., Ltd., Suwon-si, Gyeonggi-do (KR)

(72) Inventors: Seongho Cho, Seoul (KR); Hong-Bin Min, Seoul (KR); Kwan-Su Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/892,276

(22) Filed: Feb. 8, 2018

(65) Prior Publication Data
US 2018/0227706 A1 Aug. 9, 2018

(30) Foreign Application Priority Data
Feb. 8, 2017 (KR) .................... 10-2017-0017459

(51) Int. Cl.
| | | |
|---|---|---|
| *H04M 1/00* | (2006.01) | |
| *H04W 4/02* | (2018.01) | |
| *H04M 1/725* | (2006.01) | |
| *A61B 5/11* | (2006.01) | |
| *A61B 5/00* | (2006.01) | |
| *A63B 24/00* | (2006.01) | |

(Continued)

(52) U.S. Cl.
CPC ........... *H04W 4/023* (2013.01); *A61B 5/0022* (2013.01); *A61B 5/1118* (2013.01);
(Continued)

(58) Field of Classification Search
CPC ........ G06F 3/017; G06F 3/0481; G06F 1/163; G06F 11/3438; H04W 4/027; H04W 4/80; H04W 4/026; H04W 4/025; H04W 4/02
(Continued)

(56) References Cited

U.S. PATENT DOCUMENTS

2009/0118100 A1 5/2009 Oliver et al.
2009/0144639 A1 6/2009 Nims et al.
(Continued)

FOREIGN PATENT DOCUMENTS

KR 10-2015-0008534 A 1/2015
KR 10-2015-0020583 A 2/2015
(Continued)

OTHER PUBLICATIONS

ISA/KR, "International Search Report and Written Opinion of the International Searching Authority," International Application No. PCT/KR2018/001712, May 23, 2018, 10 pages.

*Primary Examiner* — Ronald Eisner

(57) ABSTRACT

This disclosure includes a method and electronic device for providing activity information of another related to an activity pattern of a user. The device includes a communication module, a sensor configured to sense a motion of a user of the device, a memory configured to store information about a first event and second event related to an activity pattern of the user, and at least one processor. The processor is configured to: acquire first activity information that is related to the motion of the user, select a corresponding one event among the first event and the second event, based at least on the first activity information, receive, from an external device, data corresponding to second activity information that is related to motions of one or more other users related to the corresponding one event, and display data corresponding to the first activity information and the data corresponding to the second activity information.

14 Claims, 32 Drawing Sheets

(51) Int. Cl.
*G06F 3/0482* (2013.01)
*H04W 4/06* (2009.01)
*G06Q 50/00* (2012.01)

(52) U.S. Cl.
CPC ..... *A63B 24/0062* (2013.01); *H04M 1/72569*
(2013.01); *H04W 4/027* (2013.01); *A61B*
*5/1112* (2013.01); *A61B 5/6898* (2013.01);
*A61B 5/7282* (2013.01); *A61B 5/742*
(2013.01); *A61B 2560/0257* (2013.01); *A61B*
*2560/0475* (2013.01); *A61B 2562/0219*
(2013.01); *A61B 2562/0223* (2013.01); *A63B*
*2024/0068* (2013.01); *G06F 3/0482* (2013.01);
*G06Q 50/01* (2013.01); *H04M 1/72583*
(2013.01); *H04W 4/06* (2013.01)

(58) Field of Classification Search
USPC ............. 455/404.1, 404.2, 456.1–457;
340/539.13, 988–996; D10/104.2
See application file for complete search history.

(56) References Cited

U.S. PATENT DOCUMENTS

| | | | |
|---|---|---|---|
| 2012/0116550 | A1 | 5/2012 | Hoffman et al. |
| 2014/0074265 | A1* | 3/2014 | Arginsky ............ A63B 71/0622 700/91 |
| 2014/0244009 | A1 | 8/2014 | Mestas |
| 2015/0081823 | A1 | 3/2015 | Gao et al. |
| 2015/0350822 | A1* | 12/2015 | Xiao ....................... H04W 4/02 455/456.1 |
| 2016/0234143 | A1* | 8/2016 | Choudhary ............. H04L 51/00 |
| 2017/0032692 | A1 | 2/2017 | Choi et al. |

FOREIGN PATENT DOCUMENTS

| | | | |
|---|---|---|---|
| KR | 10-2015-0025012 A | 3/2015 | |
| KR | 10-1560954 B1 | 10/2015 | |
| WO | WO-2013074939 A8 * | 12/2013 | ......... A63B 71/0622 |

\* cited by examiner

METHOD FOR PROVIDING ACTIVITY INFORMATION OF OTHER RELATED TO ACTIVITY PATTERN OF USER AND ELECTRONIC DEVICE THEREOF

CROSS-REFERENCE TO RELATED APPLICATIONS

This application is based on and claims priority under 35 U.S.C. § 119 to Korean Patent Application No. 10-2017-0017459, filed on Feb. 8, 2017, in the Korean Intellectual Property Office, the disclosure of which is incorporated by reference herein in its entirety.

TECHNICAL FIELD

Various embodiments of the disclosure relate to a method for providing activity information of another related to an activity pattern of a user and an electronic device thereof.

BACKGROUND

As portable electronic devices such as smartphones have high performance more and more, various services are being provided through the electronic devices. For example, a service area is expanding into more complicated services such as a game, a messenger, document editing, image/video playing and editing, etc., further to a basic service such as phone call, text sending, etc.

Further, with the miniaturization and high performance of various measuring equipment, the portable electronic devices got to be able to record information about a user activity and exercise. Accordingly to this, to promote a user health, a service of measuring and recording information about activity and exercise is being provided. Furthermore, this service is providing a service for maintaining the user health through mutual rivalry and encouragement which are based on social relation.

The above information is presented as background information only to assist with an understanding of the present disclosure. No determination has been made, and no assertion is made, as to whether any of the above might be applicable as prior art with regard to the present disclosure.

SUMMARY

Various embodiments of the disclosure may provide a method for recommending a rival through an exercise related application and an electronic device thereof.

Various embodiments of the disclosure may provide a method for identifying activity information for recommendation and an electronic device thereof.

Various embodiments of the disclosure may provide a method for recommending a rival, based on activity information, and an electronic device thereof.

Various embodiments of the disclosure may provide a method for recommending a rival, based on location information or place information, and an electronic device thereof.

Various embodiments of the disclosure may provide a method for recommending a rival, based on communication history information, and an electronic device thereof.

Various embodiments of the disclosure may provide a method for recommending a virtual user as a rival, based on pre-stored information, and an electronic device thereof.

Various embodiments of the disclosure may provide a method for conducting rivalry within a group in an exercise related application and an electronic device thereof.

Various embodiments of the disclosure may provide a method for conducting rivalry among groups in an exercise related application and an electronic device thereof.

According to various embodiments of the disclosure, an electronic device may include a communication module, at least one sensor configured to sense a motion of a user of the electronic device, a memory configured to store information about a first event and second event related to an activity pattern of the user of the electronic device, and a processor. The processor may be set to acquire first activity information which is related to the motion of the user of the electronic device, by using the sensor, select corresponding one event among the first event and the second event, based at least on the first activity information, receive, from an external device, data corresponding to second activity information which is related to motions of one or more other users related to the corresponding one event, by using the communication module, and display data corresponding to the first activity information and the data corresponding to the second activity information, by using a display operatively coupled with the electronic device.

According to various embodiments of the disclosure, an electronic device may include a communication module, a memory configured to store activity information about a first event and second event of a plurality of users, and a processor. The processor may be set to receive information about at least one event selected among the first event and the second event from an external device, through the communication module, select at least one user among the plurality of users, based at least on the information about the at least one event, and transmit information corresponding to the selected user among the activity information, to the external device through the communication module.

According to various embodiments of the disclosure, a computer-readable recording medium including a plurality of instructions is provided. The plurality of instructions may be set to, in response to being executed by the processor, enable the processor to perform sensing a motion of a user of the electronic device through at least one sensor, storing, in a memory, information about a first event and a second event related to an activity pattern of the user of the electronic device, and acquiring first activity information related to the motion of the user of the electronic device by using the at least one sensor, selecting corresponding one event among the first event and the second event, based at least on the first activity information, receiving, from an external device, data corresponding to second activity information which is related to motions of one or more other users related to the corresponding one event, by using the communication module, and displaying data corresponding to the first activity information and the data corresponding to the second activity information by using a display operatively coupled with the electronic device.

According to various embodiments of the disclosure, an operation method of an electronic device may include acquiring first activity information, transmitting first data to an external device, receiving, from the external device, data corresponding to second activity information which is related to motions of one or more other users, and displaying data corresponding to the first activity information and the data corresponding to the second activity information.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
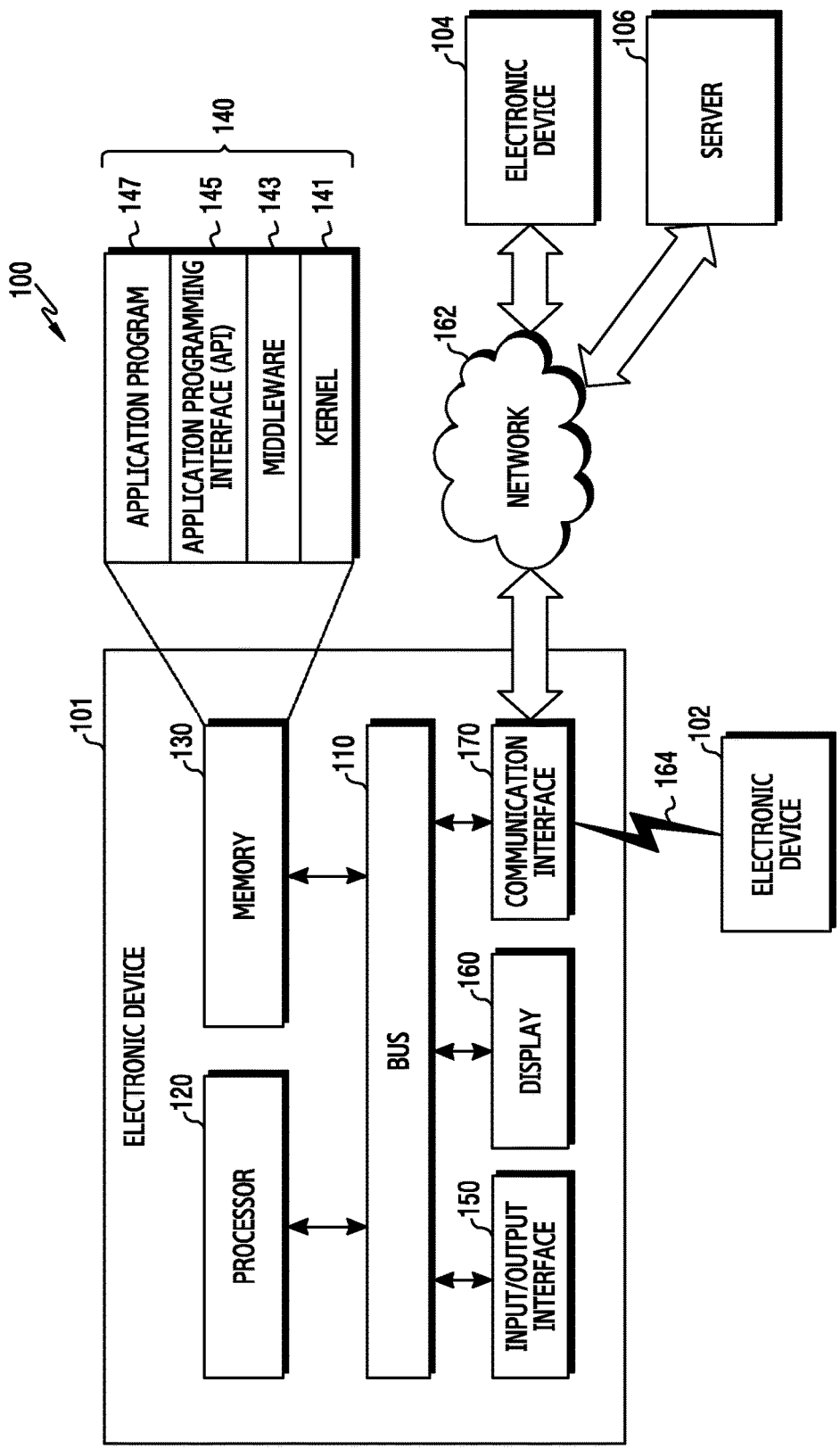
FIG. 1 illustrates an electronic device within a network environment in various embodiments of the disclosure.

FIGS. 1 through 26, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Hereinafter, various example embodiments of the present disclosure will be described with reference to the accompanying drawings. However, it should be understood that there is no intent to limit the present disclosure to the particular forms disclosed herein; rather, the present disclosure should be understood to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposed between them. In contrast, it may be understood that when an element (e.g., first element) is referred to as being "directly connected," or "directly coupled" to another element (second element), there are no element (e.g., third element) interposed between them.

The expression "configured to" used in the present disclosure may be used interchangeably with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may refer to a situation in which that the device, together with other devices or components, "is able to". For example, the phrase "processor adapted (or configured) to perform A, B, and C" may refer, for example, to a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even where the term is defined in the present disclosure, it should not be interpreted to exclude embodiments of the present disclosure.

An electronic device according to various example embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device, or the like, but is not limited thereto. According to various example embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit), or the like, but is not limited thereto.

According to some example embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HOMESYNC, APPLE TV, or GOOGLE TV, a game console (e.g., XBOX and PLAYSTATION), an electronic dictionary, an electronic key, a camcorder, and an electronic photo frame, or the like, but is not limited thereto.

According to another example embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.), or the like, but is not limited thereto.

According to some example embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter), or the like, but is not limited thereto. The electronic device according to various example embodiments of the present disclosure may be a combination of one or more of the aforementioned various devices. The electronic device according to some embodiments of the present disclosure may be a flexible device. Further, the electronic device according to an example embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 is a diagram illustrating an example network environment including an electronic device according to various example embodiments of the present disclosure.

An electronic device 101 within a network environment 100, according to various embodiments, will be described with reference to FIG. 1. The electronic device 101 may include a bus 110, a processor (e.g., including processing circuitry) 120, a memory 130, an input/output interface (e.g., including input/output circuitry) 150, a display 160, and a communication interface (e.g., including communication circuitry) 170. According to an example embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include various processing circuitry, such as, for example, and without limitation, one or more of a dedicated processor, a Central Processing Unit (CPU), an Application Processor (AP), and a Communication Processor (CP). The processor 120 may carry out, for example, calculation or data processing relating to control and/or communication of at least one other component of the electronic device 101. An operation of processing (or controlling) the processor 120 according to various example embodiments will be described below in detail with reference to the accompanying drawings.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS). The memory 130 may include a computer readable recording medium having a program recorded thereon to execute the method according to various example embodiments in the processor 120.

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data.

Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the application programs 147 control functions provided from the kernel 141 or the middleware 143, and may include, for example, at least one interface or function (e.g., instruction) for file control, window control, image processing, character control, and the like.

The input/output interface 150, for example, may include various input/output circuitry and function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a Micro Electro Mechanical Systems (MEMS) display, and an electronic paper display, or the like, but is not limited thereto. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may include various communication circuitry and may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106).

The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164. The short-range communication 164 may include at least one of, for example, WIFI, BLUETOOTH, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS).

The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various example embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
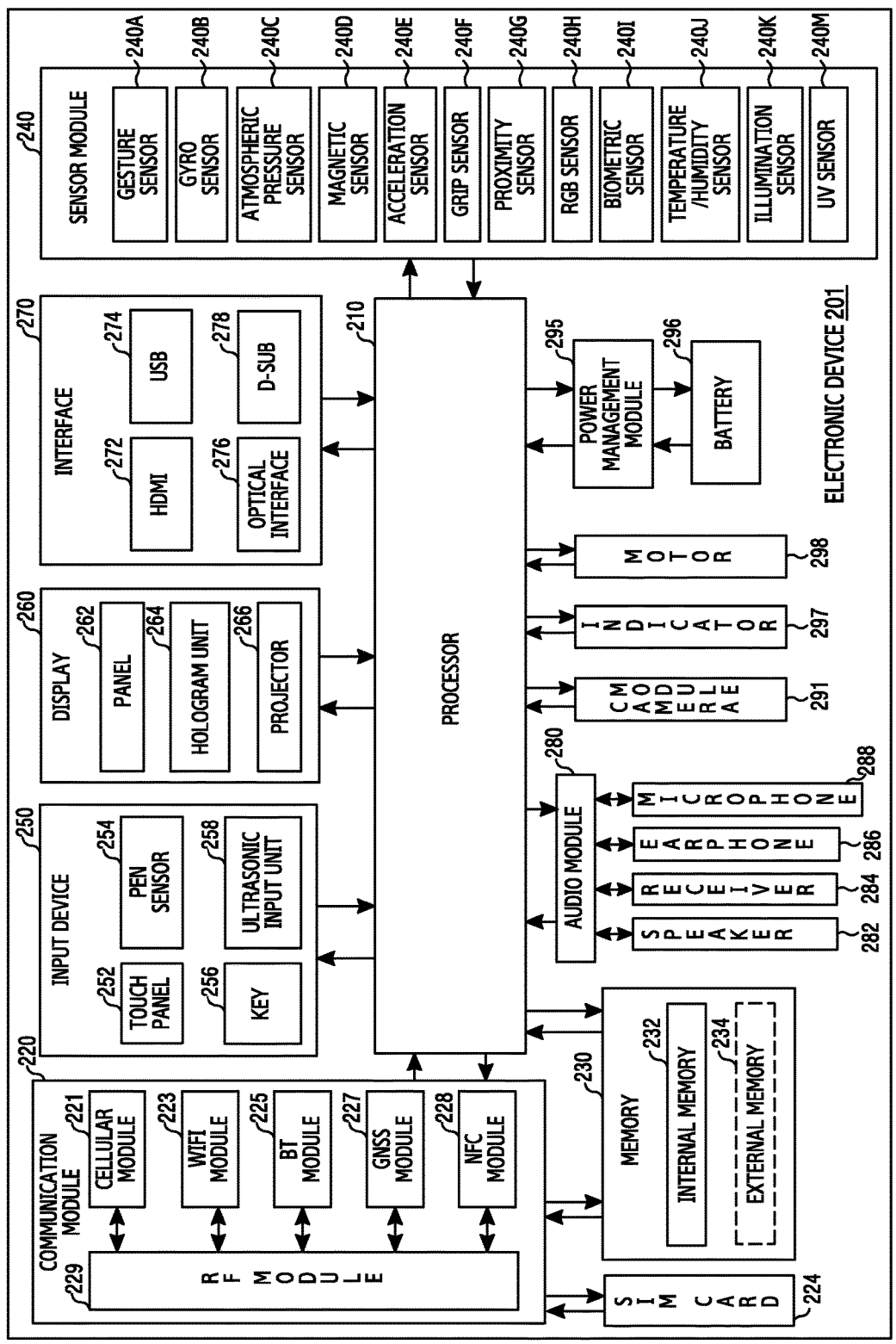
FIG. 2 illustrates a block diagram of an electronic device according to various embodiments of the disclosure.

FIG. 2 is a block diagram illustrating an example electronic device according to various example embodiments of the present disclosure.

The electronic device 201 may include, for example, all or a part of the electronic device 101 illustrated in FIG. 1. The electronic device 201 may include one or more processors (e.g., including processing circuitry) 210 (e.g., Application Processors (AP)), a communication module (e.g., including communication circuitry) 220, a Subscriber Identification Module (SIM) 224, a memory 230, a sensor module 240, an input device (e.g., including input circuitry) 250, a display 260, an interface (e.g., including interface circuitry) 270, an audio module 280, a camera module (e.g., including a camera) 291, a power management module 295, a battery 296, an indicator 297, and a motor 298.

The processor 210 may include various processing circuitry configured to control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include various communication circuitry, such as, for example, and without limitation, a cellular module 221, a WIFI module 223, a BT module 225, a GNSS module 227 (e.g., a GPS module, a Glonass module, a Beidou module, or a Galileo module), an NFC module 228, and a Radio Frequency (RF) module 229.

The cellular module 221, for example, may provide a voice call, a video call, a text message service, or an Internet service through a communication network. According to an embodiment of the present disclosure, the cellular module 221 may distinguish and authenticate the electronic device 201 in a communication network using the subscriber identification module 224 (for example, the SIM card). According to an embodiment of the present disclosure, the cellular module 221 may perform at least some of the functions that the processor 210 may provide. According to an embodiment of the present disclosure, the cellular module 221 may include a communication processor (CP).

For example, each of the WIFI module 223, the BT module 225, the GNSS module 227, and the NFC module 228 may include a processor for processing data transmitted/received through a corresponding module. According to an embodiment of the present disclosure, at least some (e.g., two or more) of the cellular module 221, the WIFI module 223, the BT module 225, the GNSS module 227, and the NFC module 228 may be included in one Integrated Chip (IC) or IC package.

The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the WIFI module 223, the BT module 225, the GNSS module 227, and the NFC module 228 may transmit/receive an RF signal through a separate RF module.

The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 and/or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like).

The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance (e.g., light) sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include various input circuitry, such as, for example, and without limitation, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266.

The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include various interface circuitry, such as, for example, and without limitation, a High-Definition Multimedia Interface (HDMI) 272, a Universal Serial Bus (USB) 274, an optical interface 276, or a D-subminiature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288.

The camera module 291 may include various circuitry including, for example, and without limitation, a camera, a device which may photograph a still image and a video, or the like. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or mediaFLO™.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
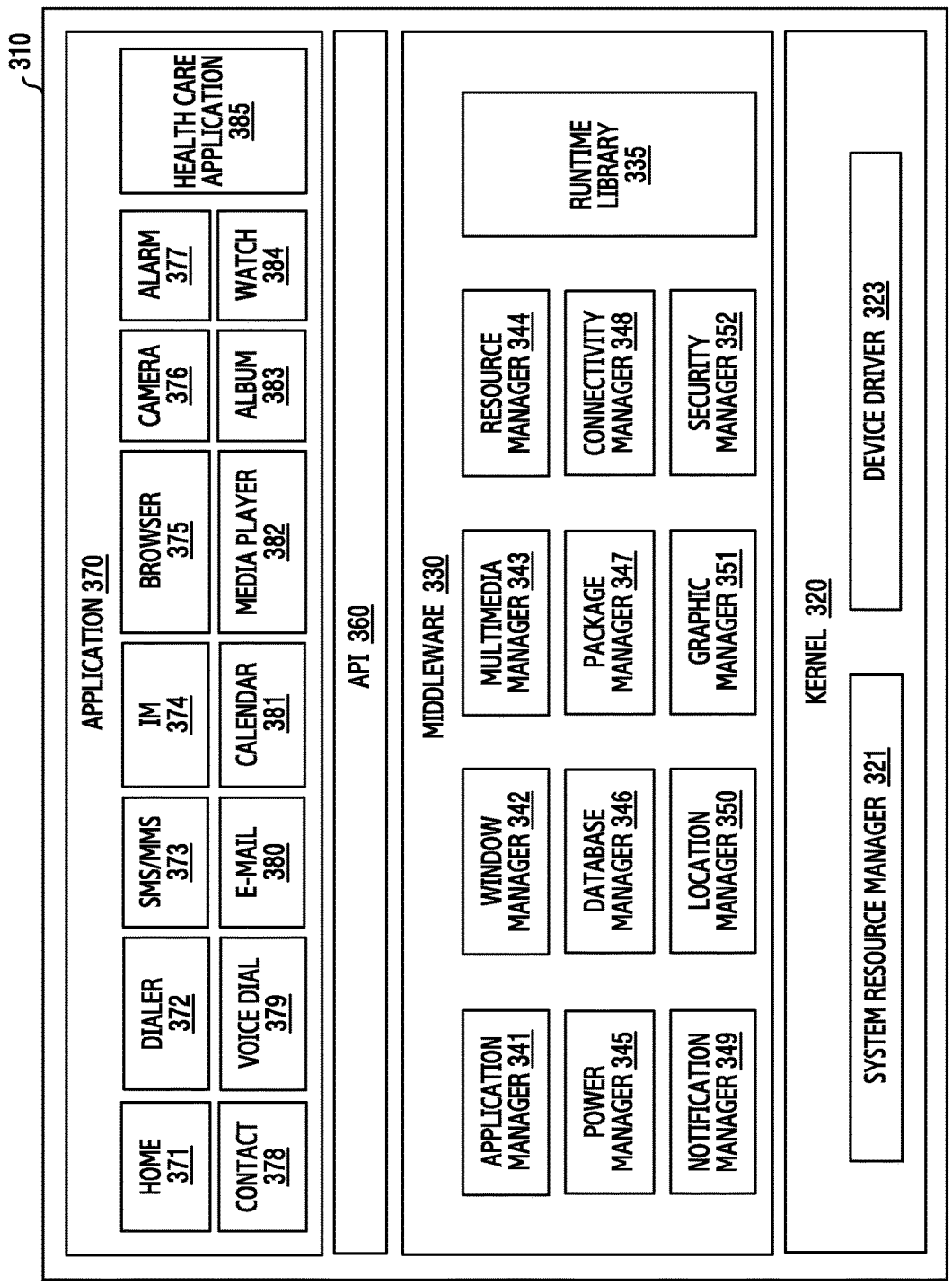
FIG. 3 illustrates a block diagram of a program module according to various embodiments of the disclosure.

FIG. 3 is a block diagram illustrating an example program module according to various example embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, ANDROID, IOS, WINDOWS, SYMBIAN, TIZEN, BADA, or the like.

The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a BLUETOOTH driver, a shared memory driver, a USB driver, a keypad driver, a WIFI driver, an audio driver, or an Inter-Process Communication (IPC) driver.

For example, the middleware 330 may provide a function required in common by the applications 370, or may provide various functions to the applications 370 through the API 360 so as to enable the applications 370 to efficiently use the limited system resources in the electronic device. According to an example embodiment of the present disclosure, the middleware 330 (e.g., the middleware 143) may include at least one of a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format required for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like required for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as WIFI or BLUETOOTH. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions required for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of ANDROID or IOS, one API set may be provided for each platform. In the case of TIZEN, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, a contact 378, a voice dial 379, an email 380, a calendar 381, a media player 382, an album 383, a watch 384. According to various example embodiments, the application 370 may include an application for providing a health care (e.g., for measuring exercise quantity or blood sugar, etc.), or environment information (e.g., providing atmospheric pressure, humidity, or temperature information).

According to an embodiment, by using at least one sensor, the health care application 385 may collect user related information, for example, information such as an exercise event of a motion, a user location, a record for each event and the like. Particularly, according to various embodiments of the disclosure, the health care application 385 may provide various functions by using information about a rival that is recommended from the server 106 or is recommended based on data pre-stored in the electronic device 101. For example, the health care application 385 may provide a person-to-person challenge service that uses first data including an exercise record, etc. recorded by measuring or automatically recognizing an activity level of the electronic device 101. Also, the health care application 385 may provide a group of users and receive the first data from electronic devices of the users, and based on this, provide a group challenge service as well.

According to various embodiments of the disclosure, the electronic device may recommend a rival in an exercise related application. For the sake of rival recommendation, location information, place information, activity information of an application user, user selection input information, etc. may be used. Various embodiments of the disclosure for recommending a rival are described below in more detail with reference to FIG. 4 to FIG. 24B.

First, for description clarity and concreteness, some terms are defined and used in the following description.

The term 'challenge' may represent rivalry that a user of the electronic device 101 conducts on the health care application 385. For example, the 'challenge' may include rivalry among users of mutually different electronic devices (e.g., the electronic device 102 or the electronic device 104), rivalry against a virtual user being based on data of the electronic device 101, rivalry among a plurality of users being based on a group, and the like. The 'challenge' may be denoted as 'contending', 'match', 'rivalry' or another term having a technological meaning equivalent to this.

The term 'rival' may represent a counterpart to which the user of the electronic device 101 conducts challenge For example, the 'rival' may include a user recommended from the server 106, a virtual user being based on data of the electronic device 101, or a user directly selected by the user of the electronic device 101. For example, the 'rival' may be a user who is located in the same place, or may be a user who has similar activity information. In another example, in case where the electronic device 101 receives a rival list from the server 106, the 'rival' may be a user who is selected from the rival list by the user of the electronic device 101.

The term 'group' is a set of users of electronic devices who use the health care application 385. In an example, the 'group' may be a set of users of a similar area being based on a location or place or may be a set of space users being based on a space on a server. According to an embodiment, user ranking may be defined through rivalry among users within a group, and group ranking may be defined through rivalry among the groups as well.

The term 'space' may represent a virtual place for specifying a condition for a rivalry state. The 'space' may be provided by the server 106, and may be selected by a user of an electronic device. The 'space' may consist of a single layer or multiple layers. For example, one space may include at least one sub space. In an example, the 'space' may be specified by an exercise event, a target level, an age, a gender, a place or a combination of them. In another example, as the group is provided, the 'space' may be provided, and the 'space' of the group provision may be in a private state.

Figure 4:
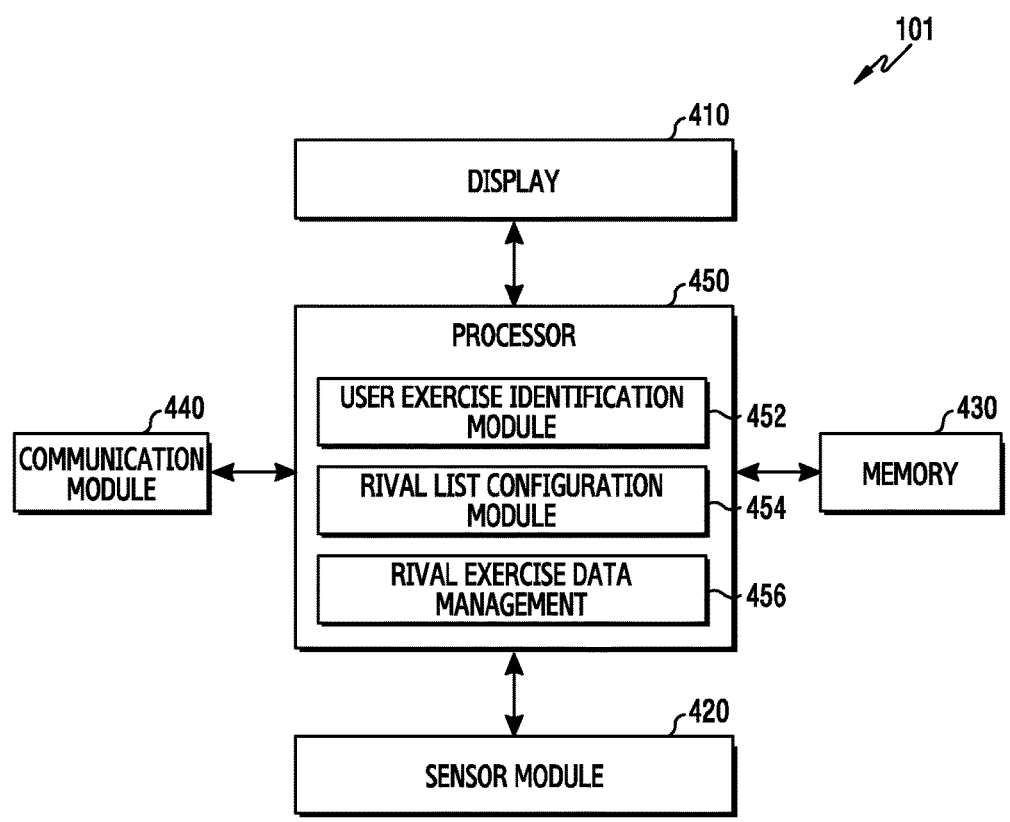
FIG. 4 illustrates a functional construction of an electronic device according to various embodiments of the disclosure.

FIG. 4 illustrates a functional construction of an electronic device according to various embodiments of the disclosure. FIG. 4 exemplifies a construction of the electronic device 101.

Referring to FIG. 4, the electronic device 101 may, for example, include a display 410, a sensor module 420, a memory 430, a communication module 440 and a processor 450 (e.g., the processor 120 of FIG. 1 or the processor 210 of FIG. 2).

The display 410 may be a device for screen display of the electronic device 101. For example, the display 410 may be comprised of at least one of an OLED (organic light emitting diode), a QLED (quantum-dot light emitting diode) and/or a LCD (liquid crystal display). The display 410 may be a constituent element corresponding to the display 160 of FIG. 1 or the display 260 of FIG. 2. According to an embodiment, the display 410 may display information on a rival recommended from the server 106 on the health care application 385. In another embodiment, the display 410 may display information related to the user of the electronic device 101 acquired from the sensor module 420. Here, the information displayed through the display 410 may be place information, first data and second data, and/or information such as a challenge result, etc.

The sensor module 420 may acquire information on a motion of the electronic device 101 or the user of the electronic device 101. The sensor module 420 may include the same or similar construction with the sensor module 240 of FIG. 2. For example, the sensor module 420 may include an acceleration sensor, and may measure an activity level including the number of steps. In another example, the sensor module 420 may include an altitude sensor. The sensor module 420 may include a motion sensor including a gyro sensor, a geomagnetic sensor, etc., besides the acceleration sensor and the altitude sensor. And, the sensor module 420 may include at least one medical sensor (e.g., a heart rate sensor) capable of measuring user's medical information. By using at least one sensor included in the sensor module 420, the electronic device 101 may acquire at least one sensor data provided according to a user motion. The electronic device 101 may identify a user exercise state (e.g., a time of exercise execution, the number of exercise execution, etc.) and a current activity state, based on the acquired at least one sensor data. For example, the electronic device 101 may identify swimming, bicycle riding, walking, hiking, etc., in addition to squat and running, based on the at least one sensor data acquired by the sensor module 420.

The memory 430 may store data such as a basic program for an operation of the electronic device 101, an application program, setting information, etc. Here, the application program may include the health care application 385. The memory 430 may include the same or similar construction with the memory 130 of FIG. 1 or the memory 230 of FIG. 2. The memory 430 may be comprised of a volatile memory, a non-volatile memory, or a combination of the volatile memory and the non-volatile memory. The memory 430 may provide stored data in response to a request of the processor 450. The memory 430 may store information on sensor data acquired through the sensor module 420, a user exercise state being based on the sensor data, and a current activity state. And, the memory 430 may store information related to a rival or rival list received from the server 106 through the communication module 440. Also, the memory 430 may store location information, place information, etc. which are acquired through the communication module 440.

The communication module 440 may perform a function of receiving a signal from an external device (e.g., the electronic device 102 or the server 106) or transmitting a signal to the external device. The communication module 440 may include the same or similar construction with the communication interface 170 of FIG. 1 or the communication module 220 of FIG. 2. For example, the electronic device 101 may receive information about a rival or rival list from the server 106 through the communication module 440. And, the electronic device 101 may transmit data such as activity information of the user of the electronic device 101 acquired through the sensor module 420, to the server 106 through the communication module 440. Also, the communication module 440 may acquire location information and place information of the electronic device 101. For example, the communication module 440 may acquire a user location through a GPS module in the form of coordinate information including a concrete latitude and longitude. In this case, the place information may be identified based on the acquired location information.

The processor 450 may control general operations of the electronic device 101. For example, the processor 450 may control screen display of the display 410, and control a measurement operation of at least one sensor module 420, and transmit received at least one sensor data to the health care application 385. For example, the processor 450 may include a user exercise identification module 452, a rival list configuration module 454 and a rival exercise data management module 456. Here, the user exercise identification module 452, the rival list configuration module 454 and the rival exercise data management module 456 are an instruction set or code which is stored in the memory 430. In detail, the user exercise identification module 452, the rival list configuration module 454 and the rival exercise data management module 456 may be an instruction/code at least temporarily resided in the processor 450 or a storage space storing the instruction/code, or may be a part of a circuitry configuring the processor 450.

The user exercise identification module 452 may identify an exercise event of a motion of the user of the electronic device 101. The user exercise identification module 452 may identify an exercise event, based on at least one sensor data acquired through at least one sensor. In an example, the user exercise identification module 452 may store, in a database, sensor data representing a specific exercise event. And, the user exercise identification module 452 may identify, as a current exercise event of the user of the electronic device 101, an exercise event having a pattern most similar with the database from acquired at least one sensor data.

The rival list configuration module 454 may configure, as a list, other users recommended for the user of the electronic device 101. In an embodiment, the processor 450 of the electronic device 101 may receive a recommendation of only one user, not a plurality of users, as a rival from the server 106, to receive data. In this case, the rival list configuration module 454 may not operate. In another embodiment, the processor 450 of the electronic device 101 may receive a plurality of user data as the rival from the server 106, and the rival list configuration module 454 may configure a plurality of users as a list. In this case, the alignment order of the list may be the same as that of a recommendation criterion for obtaining the plurality of users.

The rival exercise data management module 456 may manage information on exercise data of a rival who is received from the server 106. In an example, the processor 450 of the electronic device 101 may receive information on a selected rival from a communication module 510 of the server 106. The received information may include exercise data of the rival. In another example, by forwarding the exercise data of the rival to the memory 430, the processor 450 of the electronic device 101 may store the exercise data of the rival in the memory 430. Also, in response to a request of the health care application 385, the rival exercise data management module 456 may read the exercise data from the memory 430, and display the exercise data through the display 410. In an embodiment, by displaying the exercise data of the rival through the display 410, the processor 450 may check whether the user of the electronic device 101 conducts challenge.

According to various embodiments of the disclosure, the electronic device may include at least one sensor configured to sense a motion of a user of the electronic device, a memory configured to store information about a first event and second event related to an activity pattern of the user of the electronic device, at least one processor coupled with the at least one sensor and memory, and a communication circuitry coupled with the at least one processor. The at least one processor may be set to acquire first activity information which is related to the motion of the user of the electronic device, by using the sensor, select corresponding one event among the first event and the second event, based at least on the first activity information, receive, from an external device, data corresponding to second activity information which is related to motions of one or more other users related to the corresponding one event, by using the communication module, and display data corresponding to the first activity information and the data corresponding to the second activity information, by using a display operatively coupled with the electronic device.

According to various embodiments of the disclosure, the at least one processor may be set to transmit, to the external electronic device, the data corresponding to the first activity information by using the communication module, before the receiving operation.

According to various embodiments of the disclosure, the at least one processor may be set to select the external electronic device related to the corresponding one event, among one or more external electronic devices being in a short distance from the electronic device, before the transmitting operation.

According to various embodiments of the disclosure, the at least one processor may be set to acquire location information of the electronic device by using the at least one sensor or communication module, and perform the selecting operation, based further on the location information.

According to various embodiments of the disclosure, the processor may be set to provide a result of comparing the data corresponding to the first activity information and the data corresponding to the second activity information, by using the display.

According to various embodiments of the disclosure, the processor may be set to designate some of the one or more other users and the user, as a first group, and designate the other of the one or more other users as a second group.

According to various embodiments of the disclosure, the at least one sensor may include at least one of an acceleration sensor, a gyro sensor, a barometer, a geomagnetic sensor, a motion sensor and a GNSS (global navigation satellite system).

According to various embodiments of the disclosure, the processor may be set to transmit, to the external electronic device, communication history information of the electronic device by using the communication module, before the receiving operation, and receive, from the external electronic device, the data corresponding to the second activity information, based further on the communication history information.

Figure 5:
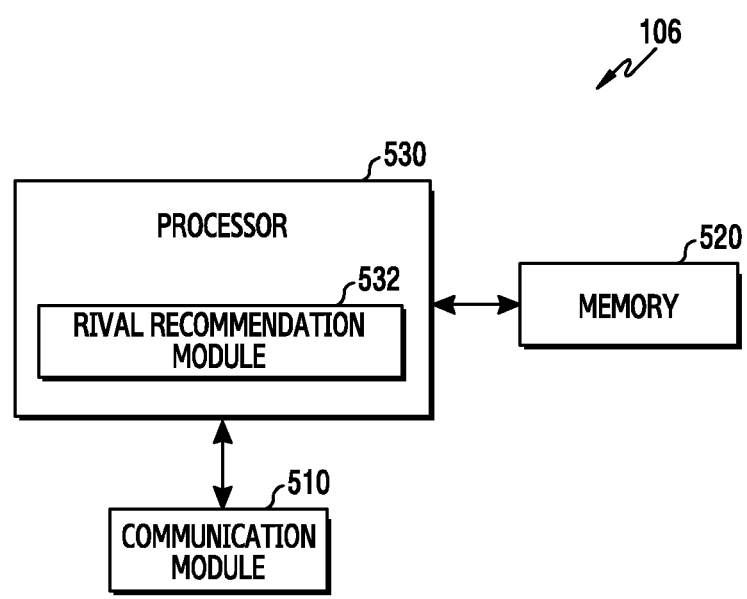
FIG. 5 illustrates a functional construction of a server according to various embodiments of the disclosure.

FIG. 5 illustrates a functional construction of a server according to various embodiments of the disclosure. FIG. 5 exemplifies a construction of the server 106.

Referring to FIG. 5, the server 106 may, for example, include the communication module 510, a memory 520 and a processor 530. For example, the processor 530 may further include a rival recommendation module 532.

The communication module 510 may receive a plurality of first data from a plurality of electronic devices (e.g., the electronic device 101 or the electronic device 102), or may transmit a plurality of second data to the plurality of electronic devices. The communication module 510 may include the same or similar construction with the communication interface 170 of FIG. 1, the communication module 220 of FIG. 2 and the communication module 440 of FIG. 4.

The memory 520 may store data such as a basic program for an operation of the server 106, an application program, etc. The memory 520 may be comprised of a volatile memory, a non-volatile memory, or a combination of the volatile memory and the non-volatile memory. For example, the memory 520 may store first data that the server 106 receives, and may read pre-stored information about a rival and second data.

The processor 530 may control general operations of the server 106. For example, by controlling the communication module 510, the processor 530 may control reception of first data, and may control transmission of user information and/or second data. In another example, by controlling the memory 520, the processor 530 may perform an operation of storing, changing and deleting first data, second data, information about a rival and the like. Additionally, the processor 530 may include the rival recommendation module 532. Here, the rival recommendation module 532, which is an instruction set or code stored in the memory 520, may be an instruction/code at least temporarily resided in the processor 530 or be a storage space storing the instruction/code, or may be a part of a circuitry configuring the processor 530.

The rival recommendation module 532 may identify a rival that the server 106 recommends to the electronic device 101. For example, the rival recommendation module 532 may include an algorithm for a plurality of recommendation criteria. Accordingly, the rival recommendation module 532 may recommend a rival according to a recommendation criterion that is selected by a user of the electronic device 101. Or, in response to the user of the electronic device 101 not selecting the recommendation criterion, the rival recommendation module 532 may arbitrarily identify a recommendation criterion and recommend a rival according to the identified recommendation criterion. In some embodiment, the rival recommendation module 532 may apply a plurality of recommendation criteria. For example, the rival recommendation module 532 may first obtain a plurality of users, based on place information, and may apply a recommendation criterion of a similar activity level to the corresponding plurality of users.

According to various embodiments of the disclosure, an electronic device may include a communication module, a memory configured to store activity information about a first event and second event of a plurality of users, and a processor. The processor may be set to receive information about at least one event selected among the first event and the second event from an external electronic device, through the communication module, select at least one user among the plurality of users, based at least on the information about the at least one event, and transmit information corresponding to the selected user among the activity information, to the external electronic device through the communication module.

According to various embodiments of the disclosure, the processor may be set to receive data related to a motion of the selected user from an electronic device of the selected user, and transmit the received data to the external device.

According to various embodiments of the disclosure, the processor may be set to select the at least one user according to a criterion selected by a user of the external device or a criterion predefined for the electronic device.

According to various embodiments of the disclosure, the at least one user may be selected, based on at least one of location information of the external device, place information, communication history information, or activity information related to the user of the external device.

According to various embodiments of the disclosure, the processor may be set to designate some of the plurality of users and a user of the external device, as a first group, and designate the other of the plurality of users as a second group.

According to various embodiments of the disclosure, the processor may be set to transmit, to the external device, data corresponding to the designated first group and second group.

Figure 6A:
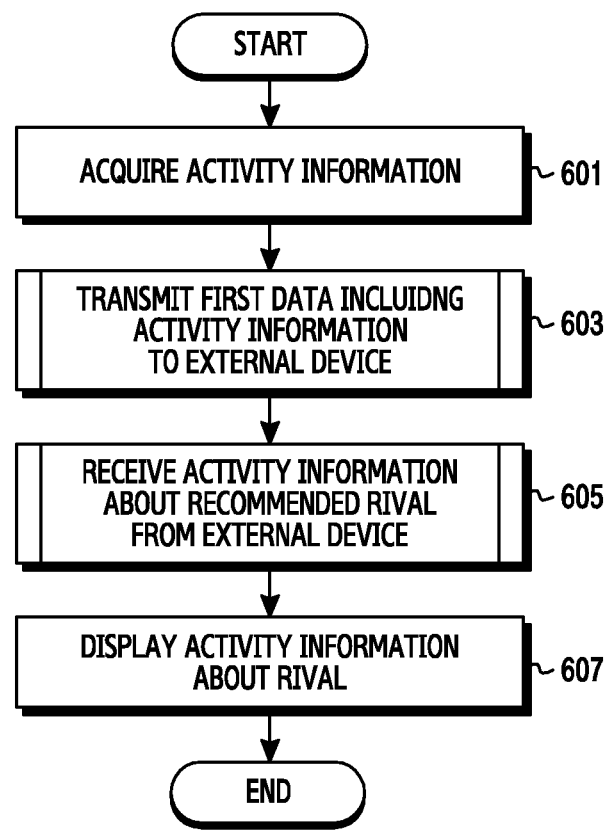
FIG. 6A illustrates a flowchart for receiving information about a recommended rival in an electronic device according to various embodiments of the disclosure.

FIG. 6A illustrates a flowchart for receiving information about a recommended rival in an electronic device according to various embodiments of the disclosure. FIG. 6A exemplifies an operation method of the electronic device 101.

Referring to FIG. 6A, in operation 601, the electronic device 101 (e.g., the processor 450) may acquire first data. The first data may include at least one of first activity information of the electronic device 101, location information, place information and communication history information. Here, the first activity information may be acquired based on sensor data related to a motion of the user of the electronic device 101. For example, the first activity information may include information about an exercise event that the user of the electronic device 101 executes and a record of the corresponding exercise event. Here, the location information may represent a location where the electronic device 101 is placed. For example, the location information includes at least one of a longitude, latitude or an address. Here, the place information is information expressing a location where the electronic device 101 is placed, in the form of POI (point of interest). The place information may include at least one of a building name, a shop name, a name of an area, or a name of a facility. For example, the electronic device 101 may measure a speed of the user of the electronic device 101 by using an acceleration sensor, and may measure an accurate change of the body of the user of the electronic device 101 by using an altitude sensor. In an embodiment, the electronic device 101 may identify an exercise event, based at least on sensor data. For example, the electronic device 101 may store a pattern of sensor data for each exercise event through the memory 430, to provide a database. The electronic device 101 may compare sensor data acquired through the sensor module 420 with the database, to identify an exercise event having the most similar pattern. Thereafter, the electronic device 101 may acquire a concrete exercise record according to the identified exercise event, and may store the exercise event and the exercise record as the first activity information.

In operation 603, the electronic device 101 (e.g., the communication module 440) may transmit the first data to an external device (e.g., the server 106). In other words, the electronic device 101 may transmit, to the external device (e.g., the server 106), at least one of the first activity information, the place information, the location information and the communication history information. In an embodiment, the electronic device 101 may transmit only the first activity information among the first data. In this case, the electronic device 101 may transmit, for example, a walk event and an exercise record on how many steps have been made, to the external device (e.g., the server 106).

In operation 605, the electronic device 101 (e.g., the communication module 440) may receive information about a recommended rival from the external device (e.g., the server 106). For example, the information about the rival may include at least one of a challenge percentage of a corresponding user, a victory and defeat record, an exercise record for each event, a mean record of the exercise record and the best record. In another embodiment, the information about the rival may include second data that includes activity information of the rival.

Figure 6B:
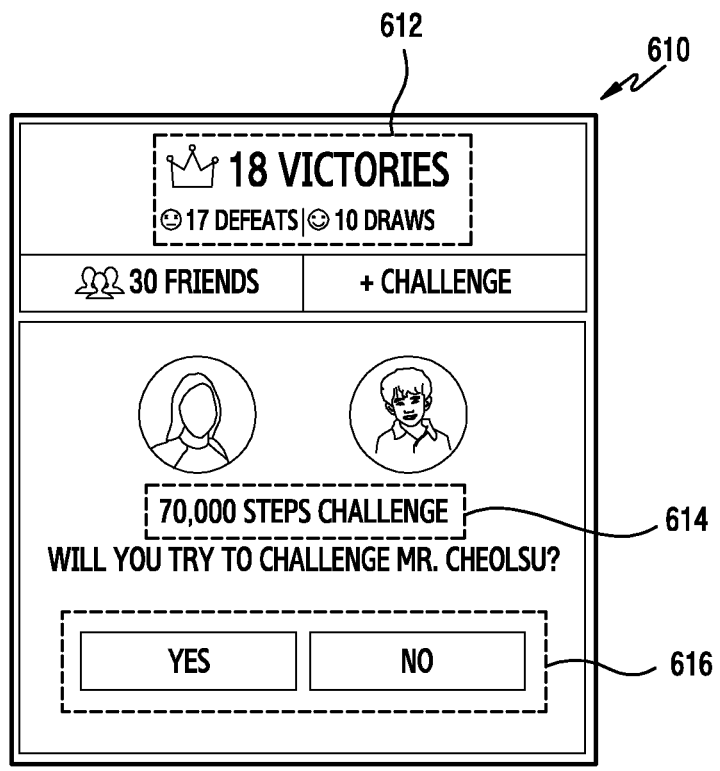
FIG. 6B illustrates an example of information about a recommended rival and challenge provision screen display in an electronic device according to various embodiments of the disclosure.

In operation 607, the electronic device 101 (e.g., the display 410) may display the information about the rival. Accordingly to this, the user of the electronic device 101 may identify the information about the rival recommended from the external device (e.g., the server 106), and may identify an exercise record for each event, etc. included in the displayed information about the rival. A UI (user interface) 610 displayed on the display 410 may be configured as in FIG. 6B. Referring to FIG. 6B, the UI 610 may include a past challenge result 612, challenge information 614, and an interface 616 inquiring challenge provision or non-provision. The past challenge result 612, a challenge record on a recommended rival, may include an accumulated record on a victory, a defeat and a draw. The challenge information 614, which is concrete information about challenge conducted with the recommended rival, may include information about an exercise event and a target level. The electronic device 101 may obtain user identification through the interface 616 inquiring challenge provision or non-provision. For example, in response to the electronic device 101 obtaining an input 'Yes', the electronic device 101 may transmit the obtained input to the external device (e.g., the server 106). The external device (e.g., the server 106) may receive the input and then, transmit a signal requiring a response to a request to an electronic device of the recommended rival. On the other hand, in response to the electronic device 101 obtaining an input 'No', the electronic device 101 may transmit the obtained input to the external device (e.g., the server 106). The external device (e.g., the server 106) may receive the input and then, transmit information about another rival to the electronic device 101.

According to various embodiments of the disclosure, an operation method of an electronic device may include acquiring first activity information, transmitting first data to an external device, receiving, from an external device, data corresponding to second activity information which is related to motions of one or more other users, and displaying data corresponding to the first activity information and the data corresponding to the second activity information.

Figure 7:
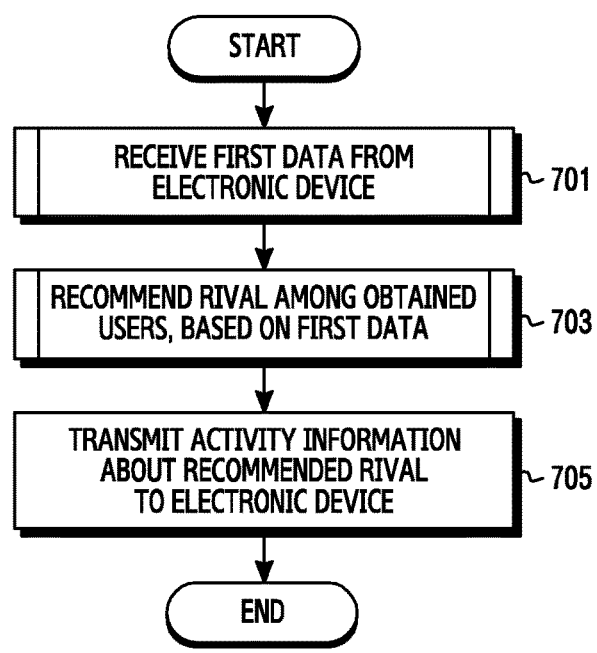
FIG. 7 illustrates a flowchart for recommending a rival in a server according to various embodiments of the disclosure.

FIG. 7 illustrates a flowchart for recommending a rival in a server according to various embodiments of the disclosure. FIG. 7 exemplifies an operation method of the server 106.

Referring to FIG. 7, in operation 701, the server 106 (e.g., the communication module 510) may receive first data from the electronic device 101. In other words, the server 106 may receive at least one of first activity information about the user of the electronic device 101, location information, place information and communication history information from the electronic device 101 through the communication module 510 of the server 106. However, the server 106 performs transmission and reception with all electronic devices which use the health care application 385, so the processor 530 of the server 106 may receive and store first data on the users of all the electronic devices.

In operation 703, the server 106 (e.g., the rival recommendation module 532) may recommend a rival among obtained users, based on the first data. Here, the server 106 may arbitrarily select a recommendation criterion through the rival recommendation module 532 of the server 106, or may be based on a recommendation criterion inputted by the user of the electronic device 101. For example, in response to the user of the electronic device 101 selecting an arbitrary third party having a similar activity level as the recommendation criterion, the server 106 may select a rival among users of the recommendation criterion which has been selected through the rival recommendation module 532 of the server 106. On the other hand, in response to there not being the recommendation criterion selected by the user of the electronic device 101, the server 106 may arbitrarily identify a recommendation criterion through the rival recommendation module 532 of the server 106, and recommend a rival among users of the identified recommendation criterion.

In operation 705, the server 106 (e.g., the communication module 510) may transmit information about the recommended rival to the electronic device 101. That is, the processor 530 of the server 106 may identify the rival recommended through the rival recommendation module 532 of the server 106, and may transmit the information about the identified rival to the electronic device 101. In some embodiment, the server 106 may transmit a rival list including all of a plurality of users of the recommendation criterion, to the electronic device 101 through the communication module 510 of the server 106. In this case, the user of the electronic device 101 may input rival selection, based on information about the plurality of users who belong to the rival list.

Figure 8A:
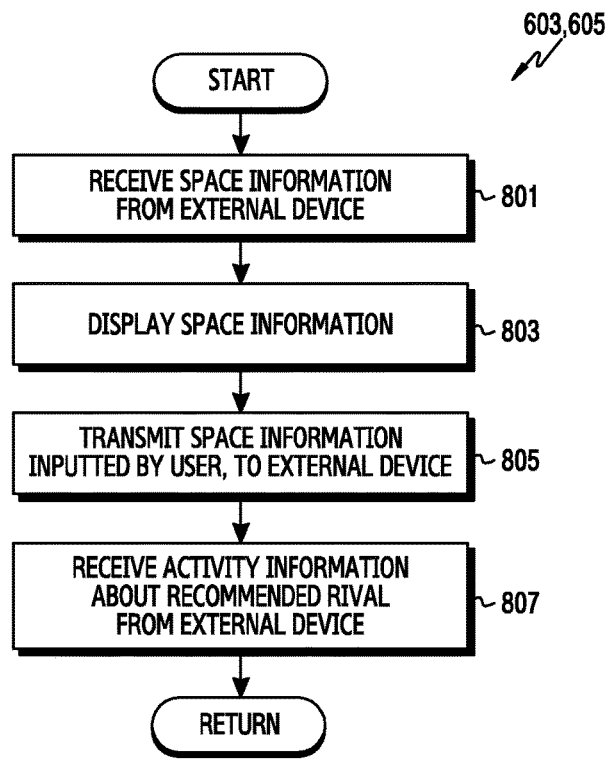
FIG. 8A illustrates a flowchart for receiving a rival who is recommended based on a space of a server, in an electronic device according to various embodiments of the disclosure.

FIG. 8A illustrates a flowchart for receiving a rival who is recommended based on a space on a server, in an electronic device according to various embodiments of the disclosure. FIG. 8A exemplifies an operation method of the electronic device 101.

Referring to FIG. 8A, in operation 801, the electronic device 101 (e.g., the communication module 440) may receive information about a space from an external device (e.g., the server 106). Here, the space may not denote a physical space, and may be a virtual space that is specified by a combination of an exercise event and a target activity level. In an example, first space may be a space for 10-thousand-step-or-more walking users, and second space may be a space for 10-kilometer-or-more running users. That is, the electronic device 101 may receive information about a space through the communication module 440 of the electronic device 101, wherein the user of the electronic device 101 may know which spaces exist on the corresponding external device (e.g., the server 106).

Figure 8B:
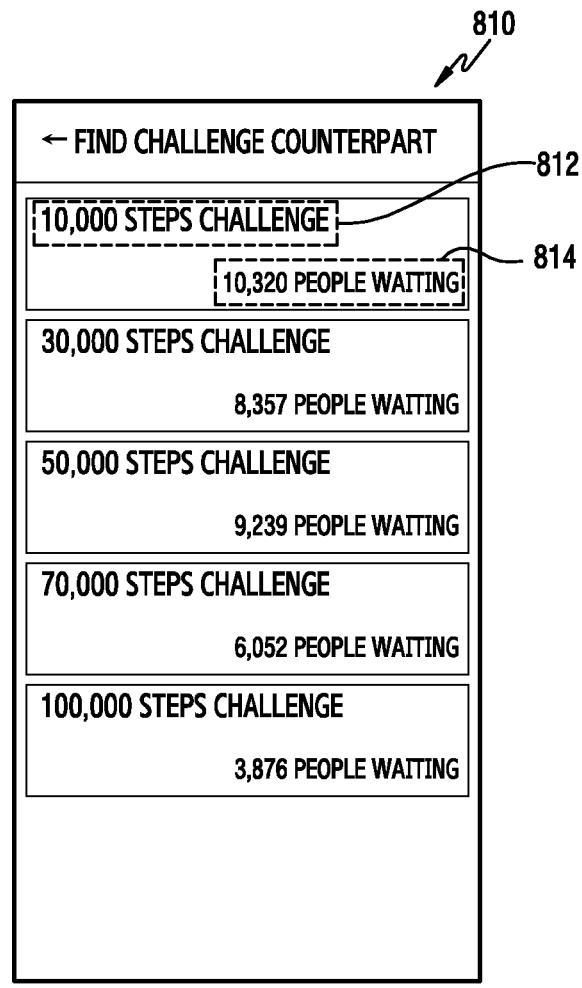
FIG. 8B illustrates an example of screen display for a space of a server in an electronic device according to various embodiments of the disclosure.

In operation 803, the electronic device 101 (e.g., the display 410) may display the information about the space. The information displayed on the display 410 may have the form of list, and concrete list display may be performed through a UI 810 of FIG. 8B. Referring to FIG. 8B, the UI 810 may include division information 812 and participated people information 814. The division information 812 may display detailed information about a space which the user of the electronic device 101 participates in. The participated people information 814 may display concretely numerically a plurality of users who are participating in each space. For example, in FIG. 8B, the division information 812 may indicate that it is a space of users who aim at 10 thousand steps in a walk event, and the participated people information 814 may indicate that 10,320 users are participating in.

Accordingly, the processor 450 of the electronic device 101 may obtain an input for a user space selection which is based on the division information 812 and the participated people information 814.

In operation 805, the electronic device 101 (e.g., the processor 450) may transmit the space information inputted by the user of the electronic device 101, to the external device (e.g., the server 106). That is, the user of the electronic device 101 may input the space selection through the UI 810 displayed on the display 410. The electronic device 101 may obtain an input, based on a user touch, etc., and may transmit the obtained input to the server 106.

Figure 8C:
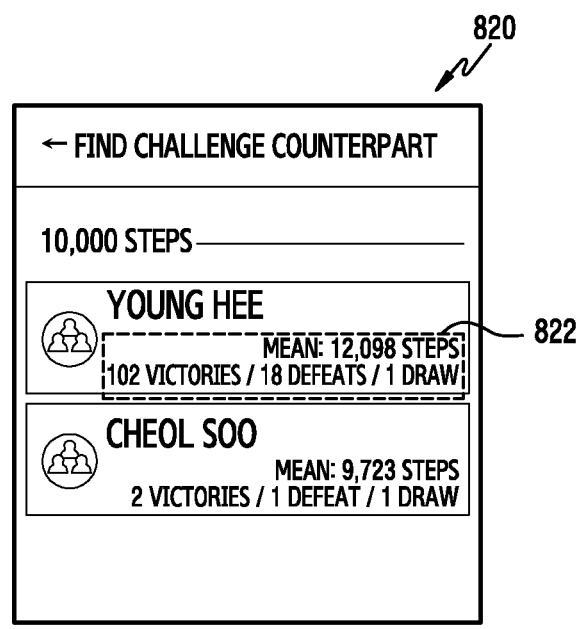
FIG. 8C illustrates an example of screen display for selecting a rival who is based on a space of a server in an electronic device according to various embodiments of the disclosure.

In operation 807, the electronic device 101 (e.g., the communication module 440) may receive information about a recommended rival from the external device (e.g., the server 106). For example, before the reception of the information about the recommended rival, the external device (e.g., the server 106) may receive a user input for a space selection, and may recommend a rival among a plurality of users who are participating in a selected space. Accordingly, the external device (e.g., the server 106) may transmit the information about the recommended rival to the electronic device 101. For example, in response to the user of the electronic device 101 selecting a 10-thousand-or-more-step walk space, the electronic device 101 may receive information about a rival among a plurality of users within the corresponding space through the communication module 440 of the electronic device 101. In an embodiment, in response to the existence of a recommendation criterion selected by the user of the electronic device 101, the electronic device 101 may receive information about a rival of a recommendation criterion among the plurality of users who are participating in the corresponding space. On the other hand, in response to the absence of the recommendation criterion selected by the user of the electronic device 101, the external device (e.g., the server 106) may receive information about a rival arbitrarily recommended among the plurality of users who are participating in the corresponding space. In another embodiment, the external device (e.g., the server 106) may receive a rival list which includes the plurality of users who are participating in the corresponding space. Referring to FIG. 8C, the electronic device 101 may receive a rival list through the communication module 440 of the electronic device 101, and display a UI 820 for a participated people list through the display 410. The UI 820 may display a plurality of users who are participating in a user input space obtained by the electronic device 101, in the form of list, and may include user information 822. Here, the user information 822 may be information associated with an arbitrary user among the plurality of users. For example, the user information 822 may have a past challenge result of a corresponding user and an activity information mean value. Referring to FIG. 8C, the electronic device 101 may display the past challenge result (e.g., 102 victories, 18 defeats, and/or 1 draw) and the activity information mean value (e.g., mean 12,098 steps in a walk event), through the user information 822. Here, the activity information mean value may be replaced with other indexes. The other indexes may be indexes such as a consumed calorie, an exercise time, the best record, etc.

Figure 9:
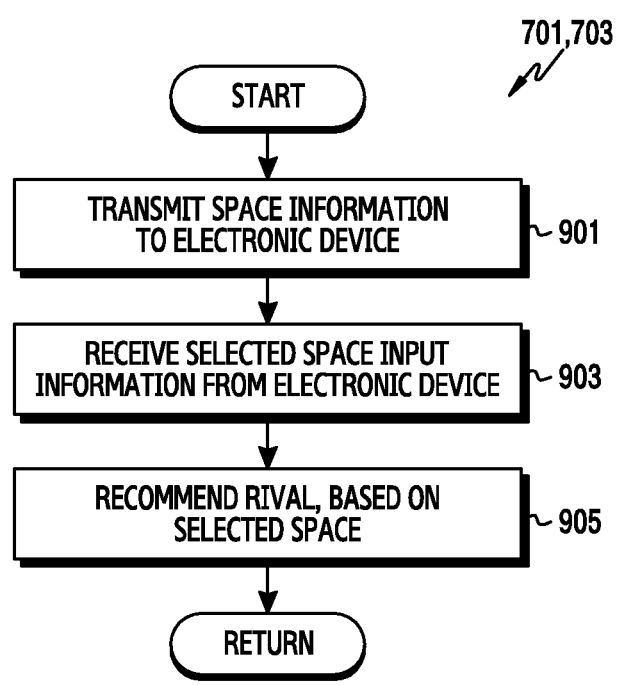
FIG. 9 illustrates a flowchart for recommending a rival, based on a space on a server, in the server according to various embodiments of the disclosure.

FIG. 9 illustrates a flowchart for recommending a rival, based on a space on a server, in the server according to various embodiments of the disclosure. FIG. 9 exemplifies an operation method of the server 106.

Referring to FIG. 9, in operation 901, the server 106 (e.g., the communication module 510) may transmit information about a space to the electronic device 101. In some embodiment, the processor 530 of the server 106 may provide spaces in advance, or may not provide the space until the user of the electronic device 101 requests for space provision. In another embodiment, the server 106 may have a plurality of spaces of a hierarchical structure.

In operation 903, the server 106 (e.g., the communication module 510) may receive input information for a selected space from the electronic device 101. That is, the electronic device 101 may receive the information about the space from the server 106, and display the received information about the space on the display 410. Accordingly, the electronic device 101 may obtain a user input for the selected space among the information about the space displayed on the display 410, and the server 106 may receive the input information about the selected space through the communication module 510 of the electronic device 101.

In operation 905, the server 106 (e.g., the rival recommendation module 532) may recommend a rival, based on the selected space. In other words, the rival recommendation module 532 of the server 106 may recommend a rival of a recommendation criterion among users who belongs to the space selected by the user of the electronic device 101. For example, in response to there being a recommendation criterion selected by the user of the electronic device 101, the server 106 may identify a rival of the corresponding recommendation criterion. On the other hand, in response to there not being the recommendation criterion selected by the user of the electronic device 101, the server 106 may arbitrarily select a recommendation criterion, and may identify a rival of the selected recommendation criterion. In an embodiment, the rival recommendation module 532 of the server 106 may recommend a rival list which includes all of a plurality of users who exist in the space selected by the user of the electronic device 101.

Figure 10:
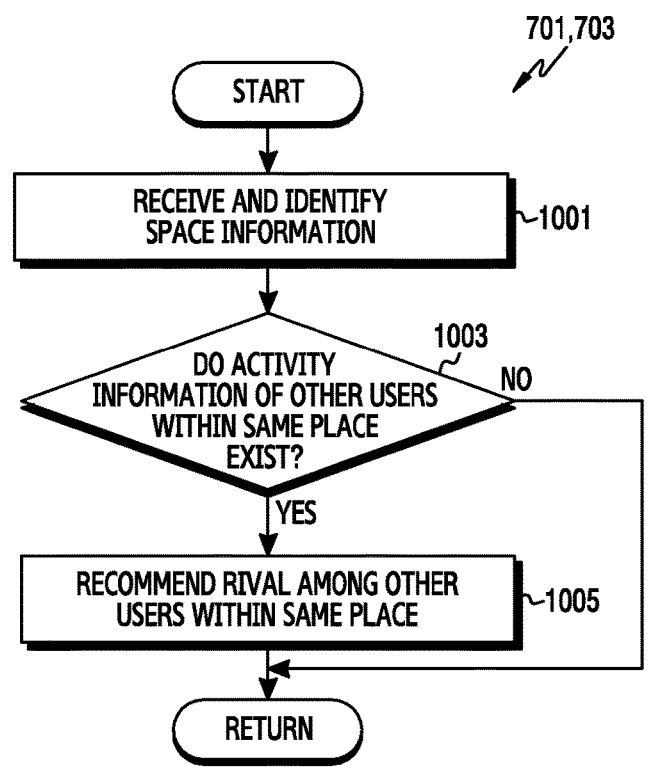
FIG. 10 illustrates a flowchart for recommending a rival, based on place information, in a server according to various embodiments of the disclosure.

FIG. 10 illustrates a flowchart for recommending a rival, based on place information, in a server according to various embodiments of the disclosure. FIG. 10 exemplifies an operation method of the server 106.

Referring to FIG. 10, in operation 1001, the server 106 (e.g., the processor 530) may receive and identify place information of the electronic device 101. For example, by using at least one of a GPS module, a WIFI module, a BLUETOOTH module, a NFC module and a cellular module that are included in the communication module 440 of the electronic device 101, the processor 450 of the electronic device 101 may acquire current location information, and may transmit the acquired location information to the server 106. Also, the processor 450 of the electronic device 101 may acquire place information where the user of the electronic device 101 is currently located, based on the pre-acquired location information, and may transmit the location information to the communication module 510 of the server 106. For example, the place information may indicate at least one POI (point of interest) and, for example, may be information such as the central park health club, the Gwanggyo lake park, the Olympic park, etc. For example, in response to the location information existing within a predetermined range of a specific place, the processor 450 of the electronic device 101 may identify that the user of the electronic device 101 is located in the corresponding specific place. Accordingly, the processor 530 of the server 106 may receive and identify the location information and place information about the user of the electronic device 101.

In operation 1003, the server 106 (e.g., the processor 530) may identify whether activity information of another user within the same place exists. In an example, in response to identifying the absence of the activity information of the another user within the corresponding place, the processor 530 of the server 106 may terminate the present algorithm. In this case, the rival recommendation module 532 of the server 106 may recommend a rival to the user of the electronic device 101 according to another recommendation criterion, not on a location basis. On the other hand, in response to identifying the existence of the activity information of the another user within the corresponding place, the processor 530 of the server 106 may recommend a rival to the user of the electronic device 101.

In operation 1005, the server 106 (e.g., the rival recommendation module 532) may recommend a rival among other users within the same place. In an example, the rival recommendation module 532 of the server 106 may provide, as a rival list, a plurality of users having activity information within the same place, and transmit information about the rival list to the electronic device 101. In another example, the rival recommendation module 532 of the server 106 may select, as a rival, one user among the plurality of users having the activity information within the same place, and transmit the information about the selected rival to the electronic device 101. In this case, the rival recommendation module 532 of the server 106 may use a recommendation criterion selected by the user of the electronic device 101 or a recommendation criterion arbitrarily selected by the server 106.

Figure 11:
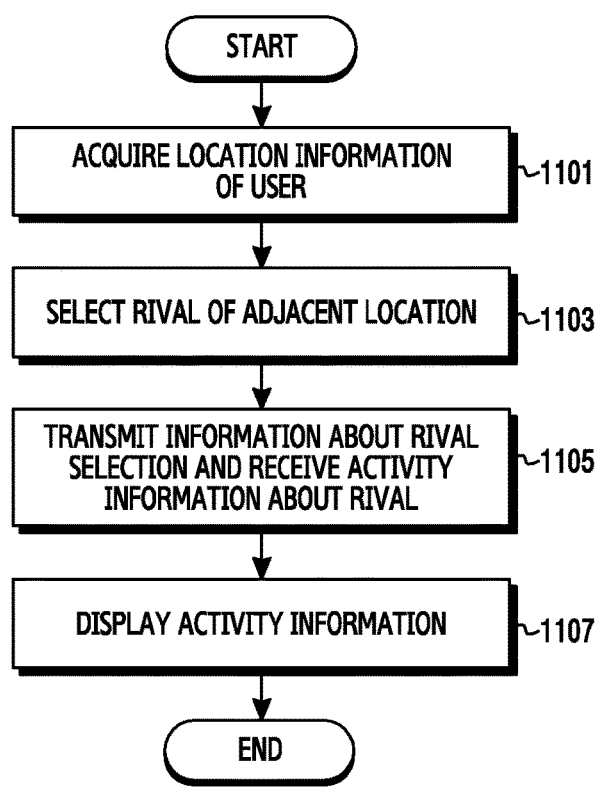
FIG. 11 illustrates a flowchart for receiving information about a recommended rival from a server, based on location information, in an electronic device according to various embodiments of the disclosure.

FIG. 11 illustrates a flowchart for receiving information about a recommended rival from a server, based on location information, in an electronic device according to various embodiments of the disclosure. FIG. 11 exemplifies an operation method of the electronic device 101.

Referring to FIG. 11, in operation 1101, the electronic device 101 (e.g., the processor 450) may acquire user location information. For example, by using the communication module 440 of the electronic device 101, the processor 450 of the electronic device 101 may receive information about a concrete latitude and longitude in which the user of the electronic device 101 is located.

In operation 1103, the electronic device 101 (e.g., the processor 450) may select a rival of an adjacent location. That is, the electronic device 101 may transmit the acquired location information to an external device (e.g., the server 106) by using the communication module 440 of the electronic device 101. And, the external device (e.g., the server 106) may transmit information about other electronic devices, which are located in locations adjacent with the electronic device 101, to the electronic device 101, based on the received location information. Accordingly to this, the processor 450 of the electronic device 101 may receive the information about the other electronic devices that are located in the adjacent locations, and identify the other electronic devices. Here, a range of the adjacent locations may have an arbitrary value given by the user of the electronic device 101, or may be another arbitrary value basically stored in the external device (e.g., the server 106). Also, the information about the other electronic devices may be information about users of the adjacent other electronic devices.

In operation 1105, the electronic device 101 (e.g., the communication module 440) may transmit information about rival selection, and receive second data about the rival. The electronic device 101 may transmit an input value for the rival selected by the user of the electronic device 101, to the external device (e.g., the server 106). In response to this, the electronic device 101 may receive the second data about the selected rival. In other words, the processor 450 of the electronic device 101 may obtain an input value for rival selection, and the external device (e.g., the server 106) may receive information about the obtained input through the communication module 510 of the server 106. The external device (e.g., the server 106) may receive the input information about the rival, and transmit a signal requesting a response to an electronic device of the corresponding rival. The external device (e.g., the server 106) may know that challenge makes progress in response to there being an approval of the selected user. Accordingly, in response to the challenge progress, the external device (e.g., the server 106) may transmit second data about the selected user to the electronic device 101 through the communication module 510 of the server 106.

In operation 1107, the electronic device 101 (e.g., the display 410) may display an exercise quantity. In other words, the electronic device 101 may receive the second data about the selected user through the communication module 440 of the electronic device 101, and may acquire the first data about the user of the electronic device 101 through the sensor module 420 of the electronic device 101. Accordingly, the processor 450 of the electronic device 101 may display the exercise quantity which is based on the first data and the second data through the display 410. In some embodiment, the display 410 of the electronic device 101 may change ranking adaptively to a current user location and exercise information, and display the changed ranking. For example, in response to the current user location being in an office, the display 410 of the electronic device 101 may display an exercise quantity and ranking for a walk event with rivals (e.g., office colleagues) of adjacent locations. In another example, in response to the current user location being in a swimming pool, the display 410 of the electronic device 101 may display an exercise quantity and ranking for a swimming event with rivals of adjacent locations.

Figure 12:
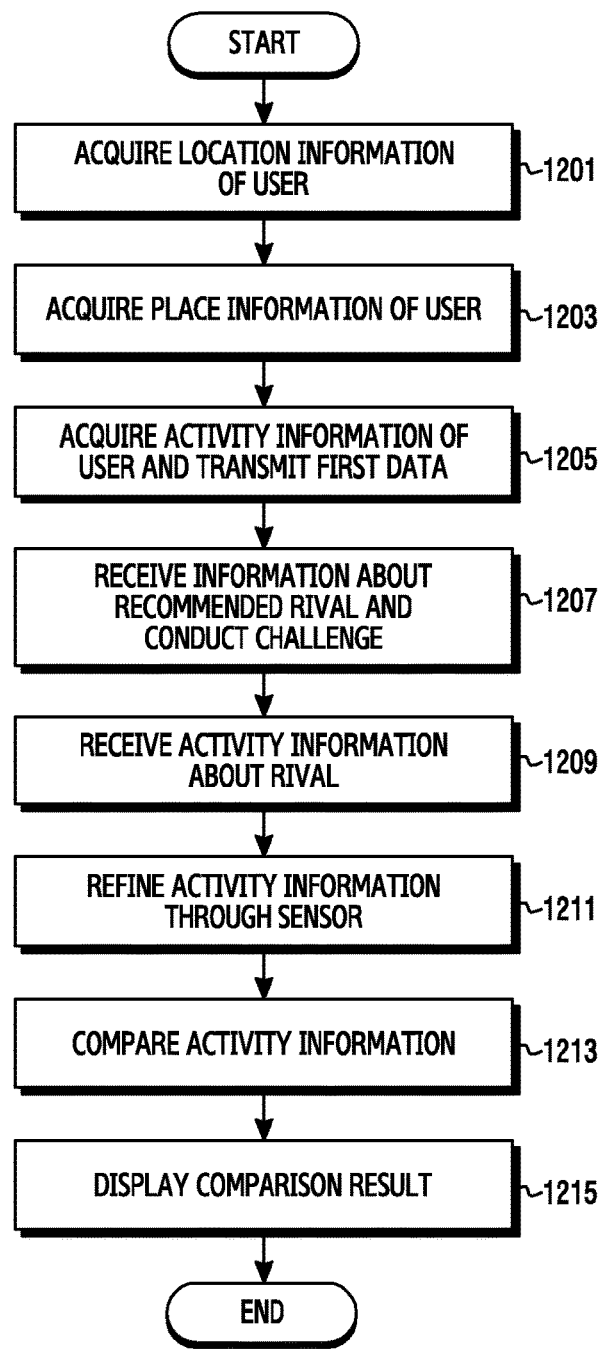
FIG. 12 illustrates a flowchart for conducting challenge to a recommended rival, based on place information, in an electronic device according to various embodiments of the disclosure.

FIG. 12 illustrates a flowchart for conducting challenge to a recommended rival, based on place information, in an electronic device according to various embodiments of the disclosure. FIG. 12 exemplifies an operation method of the electronic device 101.

Referring to FIG. 12, in operation 1201, the electronic device 101 (e.g., the processor 450) may acquire user location information. In an embodiment, in response to the health care application 385 being executed, the processor 450 of the electronic device 101 may acquire the location information. In this case, a battery consumption level may decrease. In another embodiment, the processor 450 of the electronic device 101 may acquire the location information every predetermined period of time. In this case, irrespective of execution or non-execution of the health care application 385, the processor 450 of the electronic device 101 may identify the location information by using the communication module 440 of the electronic device 101 every predetermined period of time. The corresponding predetermined period of time may be a preset value, and may be a value set by the user of the electronic device 101.

In operation 1203, the electronic device 101 (e.g., the processor 450) may identify user place information. In other words, the processor 450 of the electronic device 101 may acquire the place information, based on pre-acquired location information. In some embodiment, the processor 450 of the electronic device 101 may fail to acquire place information corresponding to current location information. In this case, the processor 450 of the electronic device 101 may display, through the display 410, a notification of notifying a failure of the place information acquisition. In another embodiment, the processor 450 of the electronic device 101 may acquire the place information, without being based on the location information. For example, the processor 450 of the electronic device 101 may acquire the place information, based on a QR code, a barcode, or a RF tag (e.g., NFC tag). In this case, since the QR code or the barcode may be arbitrarily printed in an arbitrary place, the processor 450 of the electronic device 101 may identify that the user of the electronic device 101 exists in a corresponding place. Or, the electronic device 101 (e.g., the processor 450) may acquire at least one image including at least one region of a place where the electronic device 101 is currently located, by using a camera module (not shown). The processor 450 of the electronic device 101 may acquire the place information, based on the acquired at least one image. For example, the processor 450 of the electronic device 101 may forward the acquired at least one image to an external device through the communication module 440 of the electronic device 101, and may receive the place information having been acquired based on the at least one image, from the external device. Or, the processor 450 of the electronic device 101 may acquire the place information through comparison between at least one data stored in a memory and the acquired at least one image as well.

In operation 1205, the electronic device 101 (e.g., the processor 450) may acquire a user activity state by using the sensor module 420 of the electronic device 101. And, the electronic device 101 (e.g., the processor 450) may transmit first data including the place information and the user activity state to the external device (e.g., the server 106) by using the communication module 440 of the electronic device 101. For example, the processor 450 may identify an accurate exercise event, by comparing sensor data acquired through the sensor module 420 of the electronic device 101 and a database stored in the memory 430. However, in the electronic device 101, a concrete exercise record may not be measured, and the activity information and the activity state may be distinguished.

In operation 1207, the electronic device 101 (e.g., the communication module 440 and the processor 450) may receive information about a recommended rival, and conduct challenge to the recommended rival. For example, the information about the recommended rival may include activity information of other users who perform the same activity as the user of the electronic device 101 in a place where the electronic device 101 is currently located. In some embodiment, the communication module 440 of the electronic device 101 may receive information about a plurality of users who have been accessed to a specific space. The processor 530 of the server 106 may previously provide a space corresponding to a specific location or specific place, regardless of a user request. The space may not denote a physical space. In response to the communication module 510 of the server 106 receiving corresponding location or corresponding place information from the user of the electronic device 101, the rival recommendation module 532 of the server 106 may recommend a rival among a plurality of users who are participating in a corresponding space. In another embodiment, the rival recommendation module 532 of the server 106 may recommend, as a rival list, users who have been registered to 'Hall of Fame' for the received location information or place information. In this case, the processor 530 of the server 106 may transmit information about all the users who have been registered to 'Hall of Fame', to the communication module 440 of the electronic device 101 through the communication module 510 of the server 106. A criterion of recommending the rival among the plurality of users may be a recommendation criterion selected by the user of the electronic device 101 or a recommendation criterion arbitrarily selected by the rival recommendation module 532 of the server 106. The user of the electronic device 101 may identify challenge progress or non-progress through the received information about the recommended rival. In an example, in response to the user of the electronic device 101 desiring to conduct challenge, the processor 450 may obtain an input for user challenge progress, and may transmit a message of a challenge progress request to the communication module 510 of the server 106 through the communication module 440 of the electronic device 101. The server 106 may transmit a message of inquiring challenge progress approval or non-approval to an electronic device of the recommended rival through the communication module 510 of the server 106. In response to the server 106 receiving a response to the approval, challenge may make progress. In another embodiment, the communication module 440 of the electronic device 101 may receive supplementary information about a place where a rival is located and information about the rival located in the place. For example, the communication module 440 of the electronic device 101 may receive a specific course of a park where jogging is much gone, and may receive information about a plurality of users who runs the corresponding course.

In operation 1209, the electronic device 101 (e.g., the communication module 440) may receive second data about the rival. That is, in response to the rival approving the challenge request, an electronic device of the rival may transmit first data of the corresponding electronic device of the rival to the server 106. And, the server 106 may transmit, as second data, first activity information among the received first data, to the electronic device 101 through the communication module 510 of the server 106. In another embodiment, rivalry may be performed based on past, not current, activity information of the rival. In this case, the second data received in operation 1209 may be previously acquired and stored activity information, not real-time acquired activity information. In this case, the server 106 may transmit the past received activity information of the rival as the second data.

In operation 1211, the electronic device 101 (e.g., the processor 450) may refine the first data through the sensor module 420 of the electronic device 101. That is, in response to challenge being initiated, the processor 450 may acquire sensor data through the sensor module 420 of the electronic device 101, and may acquire a concrete exercise record by interpreting the sensor data according to an exercise event. Accordingly, the processor 450 may refine the first data through first activity information of challenge progress.

In operation 1213, the electronic device 101 (e.g., the processor 450) may compare the first data and the second data. For example, the processor 450 may compare first activity information included in the first data and second activity information included in the second data of the rival. For example, in response to receiving information about a specific course of a park and information about the rival through the communication module 440 of the electronic device 101, the processor 450 may compare activity information which user most fast runs the corresponding course.

In operation 1215, the electronic device 101 (e.g., the display 410) may display the comparison result. The display 410 may display a concrete numerical value, together with the comparison result, based on the first activity information and the second activity information, or simply display being in victory or defeat. Through this, the user of the electronic device 101 may know a challenge progress situation in real-time.

Figure 13:
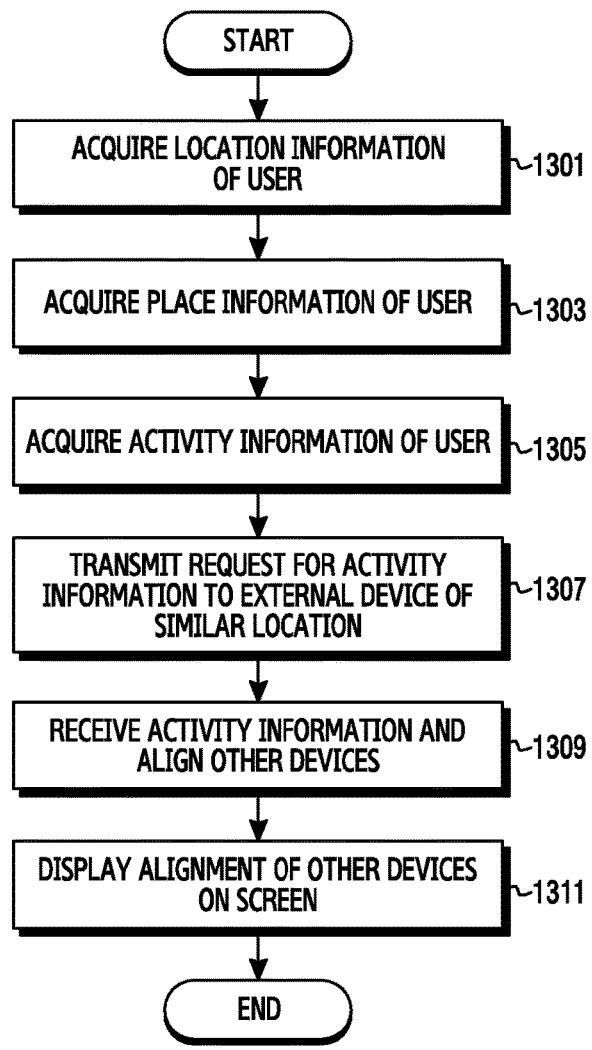
FIG. 13 illustrates a flowchart for conducting challenge to another electronic device, based on place information, in an electronic device according to various embodiments of the disclosure.

FIG. 13 illustrates a flowchart for conducting challenge to another electronic device, based on place information, in an electronic device according to various embodiments of the disclosure. FIG. 13 exemplifies an operation method of the electronic device 101.

Referring to FIG. 13, in operation 1301, the electronic device 101 (e.g., the processor 450) may acquire user location information. For example, the electronic device 101 may acquire coordinate information about an accurate latitude and longitude where the user of the electronic device 101 is located through the communication module 440 of the electronic device 101.

In operation 1303, the electronic device 101 (e.g., the processor 450) may acquire user place information. The processor 450 of the electronic device 101 may acquire place information, based on pre-acquired location information. For example, in response to the existence of an arbitrary place including the pre-acquired location information, the processor 450 of the electronic device 101 may identify that the user of the electronic device 101 is located in a corresponding place. In another example, the processor 450 of the electronic device 101 may acquire the place information through a QR code, a barcode or a RF tag (e.g., a NFC tag) as well. In response to acquiring the location information from the QR code, the barcode or the RF tag physically printed in the arbitrary place, the processor 450 of the electronic device 101 may identify that the user of the electronic device 101 is located in the corresponding place, without being based on analysis through the location information.

In operation 1305, the electronic device 101 (e.g., the processor 450) may acquire user activity information. In other words, the processor 450 of the electronic device 101 may compare sensor data acquired through the sensor module 420 of the electronic device 101 and a database stored in the memory 430, to identify an exercise event, and may analyze the sensor data according to the identified exercise event, to identify a concrete exercise record. Accordingly to this, the processor 450 of the electronic device 101 may store, in the memory 430, the identified exercise event and exercise record as the activity information.

In operation 1307, the electronic device 101 (e.g., the communication module 440) may transmit an activity information request to an electronic device of a similar location. In some embodiment, the electronic device 101 may receive information about electronic devices which are in a similar location, from the external device (e.g., the server 106) through the communication module 440 of the electronic device 101. The communication module 510 of the external device (e.g., the server 106) may receive and store respective first data from all electronic devices that use the health care application 385. Accordingly, information about electronic devices which belong to an adjacent location or the same place may be transmitted to the communication module 440 of the electronic device 101 through the communication module 510 of the external device (e.g., the server 106). In another embodiment, the electronic device 101 may request activity information according to direct coupling between devices through the communication module 440 of the electronic device 101 as well. For example, the electronic device 101 may use a short-range communication module such as a NFC module and/or a BLUETOOTH module. In this case, although the electronic device 101 does not receive information about an electronic device of an adjacent location from the communication module 510 of the external device (e.g., the server 106) through the communication module 440 of the electronic device 101, the electronic device 101 may request activity information to another electronic device. In another example, the electronic device 101 may request the activity information to another electronic device accessed to the same WIFI module through the communication module 440 of the electronic device 101. Also, the electronic device 101 may recognize the QR code or barcode displayed on a display of another electronic device or make a RF tag (e.g., a NFC tag) to contact with another electronic device through the communication module 440 of the electronic device 101, to request the activity information as well. In summary, the electronic device 101 may request the activity information to another electronic device, without going via the communication module 510 of the external device (e.g., the server 106), through the communication module 440 of the electronic device 101.

In operation 1309, the electronic device 101 (e.g., the processor 450) may perform reception of activity information and alignment of other devices. In response to the activity information request, the electronic device 101 may receive activity information of another electronic device from another electronic device which is in a similar location through the communication module 440 of the electronic device 101. In an embodiment, in response to there being another electronic device which has rejected the activity information request, the processor 450 of the electronic device 101 may perform an operation of aligning by only activity information received from other electronic devices which have approved the activity information request. The activity information may include information about an exercise event and an exercise record, and the processor 450 of the electronic device 101 may perform alignment of other devices according to the order of an exercise record of each exercise event.

In operation 1311, the electronic device 101 (e.g., the display 410) may display the alignment of other devices on a screen of the electronic device 101. For example, the processor 450 of the electronic device 101 may distinguish an exercise event into walking, running, swimming, squat, etc., and may present a user exercise record of each event on a per-ranking basis.

Figure 14:
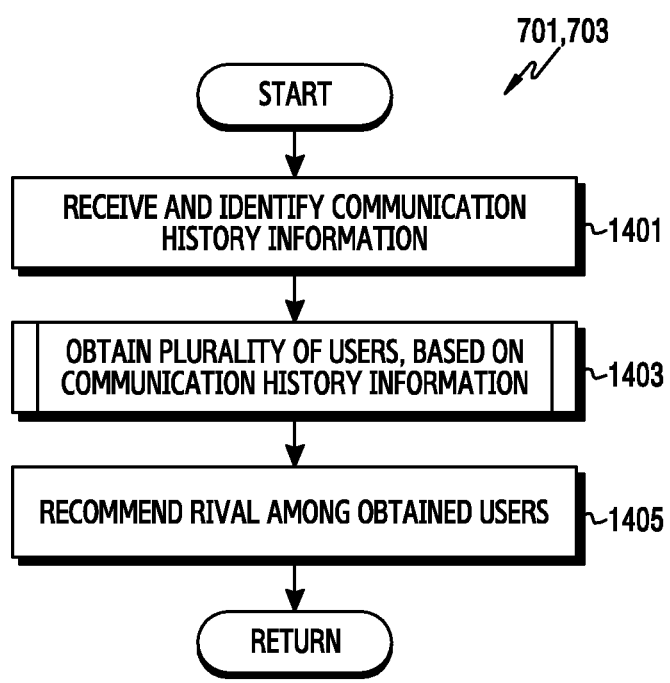
FIG. 14 illustrates a flowchart for recommending a rival, based on communication history information, in a server according to various embodiments of the disclosure.

FIG. 14 illustrates a flowchart for recommending a rival, based on communication history information, in a server according to various embodiments of the disclosure. FIG. 14 exemplifies an operation method of the server 106.

Referring to FIG. 14, in operation 1401, the server 106 (e.g., the communication module 510 and the processor 530) may receive communication history information from the electronic device 101 and identify the received communication history information. For example, the server 106 may receive first data from each electronic device through the communication module 510 of the server 106. The first data may include the communication history information. Here, the communication history information may include at least one of information on a phone book stored in each electronic device, a call list, a text message list, account information, a friend within an account, a mail address book, a friend on a SNS (social network service), and a plurality of users related to the user of the electronic device 101. In some embodiment, the user of the electronic device 101 may not transmit specific information among the communication history information according to a need of private information protection. In this case, the processor 530 of the server 106 may acquire only the remnant information excepting the specific information. In another embodiment, in response to failing to acquire the communication history information from the electronic device 101, the rival recommendation module 532 of the server 106 may execute a rival recommendation algorithm of another recommendation criterion, without being based on the communication history information as well.

In operation 1403, the server 106 (e.g., the processor 530) may obtain a plurality of users which are based on the communication history information. In an example, the processor 530 of the server 106 may identify a group of company colleagues, families, school friends, etc., of a phone book among the communication history information, and may obtain a plurality of users who belong to the corresponding group. In another example, the processor 530 of the server 106 may identify a call list among the communication history information, and may obtain a plurality of users who exist on the corresponding call list.

In operation 1405, the server 106 (e.g., the rival recommendation module 532) may recommend a rival among the obtained users. That is, the rival recommendation module 532 of the server 106 may recommend a rival among the obtained plurality of users, based on a recommendation criterion. In an example, the rival recommendation module 532 of the server 106 may recommend a rival list which includes all of the obtained plurality of users. In another example, the rival recommendation module 532 of the server 106 may recommend one of the obtained plurality of users, as a rival, according to a recommendation criterion. In this case, the recommendation criterion may be a recommendation criterion selected by the user of the electronic device 101, or may be a recommendation criterion arbitrarily selected by the rival recommendation module 532 of the server 106.

Though not illustrated, in some embodiment, the rival recommendation module 532 of the server 106 may include a plurality of users of a SNS and phone book on a rival list all the time. This may be applied even when a recommendation criterion selected by the rival recommendation module 532 of the server 106 or the user of the electronic device 101 is different from a criterion being based on the communication history information. For example, a rival list including a plurality of users obtained based on place information may include a plurality of users existing in a SNS and phone book of the user of the electronic device 101.

Figure 15:
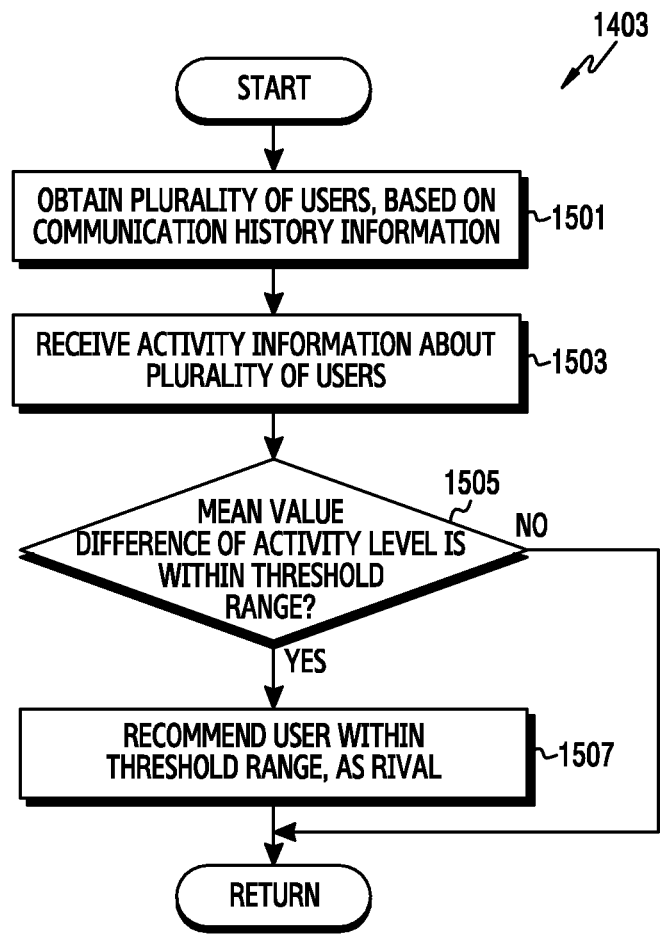
FIG. 15 illustrates a flowchart for recommending a rival having a similar activity level, based on communication history information, in a server according to various embodiments of the disclosure.

FIG. 15 illustrates a flowchart for recommending a rival having a similar activity level, based on communication history information, in a server according to various embodiments of the disclosure. FIG. 15 exemplifies an operation method of the server 106.

Referring to FIG. 15, in operation 1501, the server 106 (e.g., the processor 530) may obtain a plurality of users which are based on communication history information. For example, the processor 530 of the server 106 may obtain a plurality of users within a specific group of a phone book among the communication history information. In another example, the processor 530 of the server 106 may obtain a plurality of users on a call list. In some embodiment, the processor 530 of the server 106 may obtain a plurality of users, based on access-granted information among the communication history information.

In operation 1503, the server 106 (e.g., the communication module 510) may receive second activity information about the plurality of users. In other words, the server 106 may receive the second activity information about the plurality of users, so as to compare an activity level of the user of the electronic device 101 and activity levels of the plurality of users being obtained based on the communication history information, through communication module 510 of the server 106. In some embodiment, the processor 530 of the server 106 may pre-store the second activity information about some of the plurality of users. In this case, the server 106 may request and receive only second activity information about the other of the plurality of users through the communication module 510 of the server 106.

In operation 1505, the server 106 (e.g., the processor 530) may identify whether an activity-level mean value difference exists within a threshold range. For example, the processor 530 of the server 106 may pre-store first activity information about the user of the electronic device 101. The server 106 may receive the second activity information about the obtained plurality of users through the communication module 510 of the server 106. The second activity information may include activity-level mean value information. Accordingly, the processor 530 of the server 106 may compare the first activity information and the second activity information, to acquire an activity-level mean value difference. In some embodiment, in response to identifying that a user whose activity-level mean value difference is within a threshold range does not exist, the processor 530 of the server 106 may terminate the present algorithm. In another embodiment, in response to identifying that the user whose activity-level mean value difference is within the threshold range exists, the processor 530 of the server 106 may perform the subsequent operation. Here, the threshold range may be inputted by the user of the electronic device 101, or may be a range value basically set to the processor 530 of the server 106.

In operation 1507, the server 106 (e.g., the rival recommendation module 532) may recommend, as a rival, the user whose activity-level mean value difference is within the threshold range. That is, the rival recommendation module 532 of the server 106 may obtain users whose activity-level mean value differences are within the threshold range, and recommend the rival among the users according to a recommendation criterion. In some embodiment, in response to one user whose activity-level mean value difference is within the threshold range, the rival recommendation module 532 of the server 106 may recommend the user as the rival. In another embodiment, in response to a plurality of users whose activity-level mean value differences are within the threshold range, the rival recommendation module 532 of the server 106 may recommend one of the plurality of users as the rival, based on at least one of recommendation criteria selected by the rival recommendation module 532 of the server 106 or the user of the electronic device 101 as well. For example, the rival recommendation module 532 of the server 106 may recommend, as the rival, a user whose least mean value difference are within the threshold range among the users. In another embodiment, the rival recommendation module 532 of the server 106 may recommend a rival list which includes all of the users whose mean value differences are within the threshold range as well.

Though not illustrated, in another embodiment, the rival recommendation module 532 of the server 106 may not be based on a mean value difference, and may perform operation, based on other indexes such as the best record, consumed calorie, an exercise time, etc. as well. In an example, in response to the consumed calorie being a criterion, the rival recommendation module 532 of the server 106 may select, as a rival, a user whose consumed calorie difference is within a threshold range.

Figure 16:
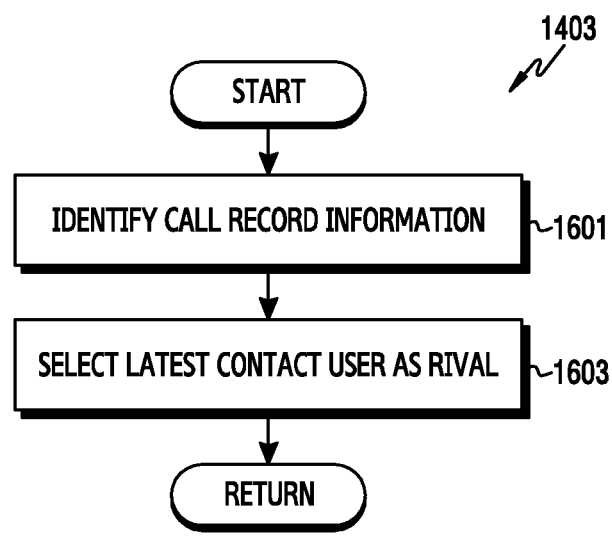
FIG. 16 illustrates a flowchart for recommending the latest contact user as a rival, based on communication history information, in a server according to various embodiments of the disclosure.

FIG. 16 illustrates a flowchart for recommending the latest contact user as a rival, based on communication history information, in a server according to various embodiments of the disclosure. FIG. 16 exemplifies an operation method of the server 106.

Referring to FIG. 16, in operation 1601, the server 106 (e.g., the processor 530) may identify call record information. In other words, the processor 530 of the server 106 may receive communication history information from the communication module 440 of the electronic device 101. The communication history information may include call record information. Accordingly, the processor 530 of the server 106 may identify the received call record information. In an embodiment, an authority for access to the call record information may not exist. In this case, the processor 530 of the server 106 may perform recommendation of another recommendation criterion.

In operation 1603, the server 106 (e.g., the rival recommendation module 532) may recommend the latest contact user as a rival. For example, the processor 530 of the server 106 may provide a call record list, based on time. The rival recommendation module 532 of the server 106 may recommend a user who is closest in time among the corresponding list, as the rival. In another example, the rival recommendation module 532 of the server 106 may recommend a user who is oldest in time among the corresponding list, as the rival.

Though not illustrated, in another embodiment, the processor 530 of the server 106 may provide a call record list which is based on a contact cycle as well. The rival recommendation module 532 of the server 106 may recommend, as a rival, a user having the shortest contact cycle among the corresponding list as well.

Figure 17:
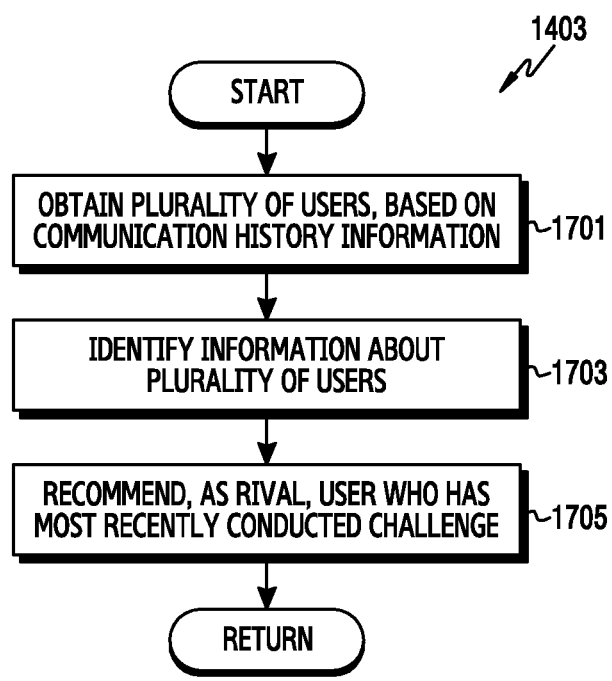
FIG. 17 illustrates a flowchart for recommending a user who has recently conducted challenge, as a rival, based on communication history information, in a server according to various embodiments of the disclosure.

FIG. 17 illustrates a flowchart for recommending a user who has recently conducted challenge, as a rival, based on communication history information, in a server according to various embodiments of the disclosure. FIG. 17 exemplifies an operation method of the server 106.

Referring to FIG. 17, in operation 1701, the server 106 (e.g., the processor 530) may obtain a plurality of users, based on communication history information. The received communication history information may include information on a phone book of the electronic device 101, a call list, a text message list, account information, a friend within an account, a mail address list, a friend on a SNS (social network service), etc. Accordingly, the processor 530 may obtain a plurality of users, based on at least one of the communication history information.

In operation 1703, the server 106 (e.g., the communication module 510 and the processor 530) may receive and identify information about the plurality of users. Here, the information about the plurality of users may include challenge progress information, etc. Accordingly, by receiving and identifying the information about the plurality of users, the processor 530 of the server 106 may check whether the obtained user has ever conducted challenge recently. In some embodiment, the processor 530 of the server 106 may pre-store the information about the plurality of users. In this case, a process of receiving the information about the plurality of users may be omitted.

In operation 1705, the server 106 (e.g., the rival recommendation module 532) may recommend a user who has recently conducted the challenge, as a rival. The rival recommendation module 532 of the server 106 may check whether challenge has ever been conducted recently, based on the information about the plurality of users, and the processor 530 of the server 106 may align the plurality of users according to a challenge progress time. Accordingly, the rival recommendation module 532 of the server 106 may identify a user who has recently conducted challenge, and recommend the corresponding user as the rival. In another example, the rival recommendation module 532 of the server 106 may identify a user who is the longest since challenge progress, and recommend the corresponding user as the rival as well. In another embodiment, the rival recommendation module 532 of the server 106 may recommend, as the rival, a user who has newly subscribed on the health care application 385. In this case, the processor 530 of the server 106 may identify subscription information about the plurality of users which is based on the communication history information as well.

Figure 18:
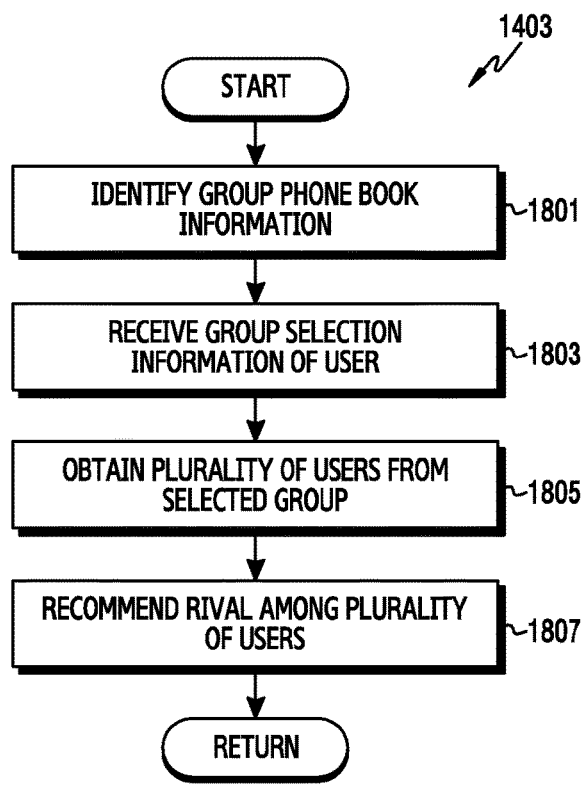
FIG. 18 illustrates a flowchart for recommending a rival in a contact group, based on communication history information, in a server according to various embodiments of the disclosure.

FIG. 18 illustrates a flowchart for recommending a rival in a contact group, based on communication history information, in a server according to various embodiments of the disclosure. FIG. 18 exemplifies an operation method of the server 106.

Referring to FIG. 18, in operation 1801, the server 106 (e.g., the processor 530) may identify phone book information. The communication module 510 of the server 106 may receive communication history information. The communication history information may include information about a phone book. Accordingly, the processor 530 of the server 106 may identify group information of a phone book of the electronic device 101. In some embodiment, in response to there not being an authority for access to the phone book, the rival recommendation module 532 of the server 106 may recommend a rival according to another recommendation criterion.

In operation 1803, the server 106 (e.g., the communication module 510) may receive group selection information of the user of the electronic device 101. The processor 450 of the electronic device 101 may obtain a user input for group selection. The obtained input may be transmitted to the communication module 510 of the server 106 through the communication module 440 of the electronic device 101.

In operation 1805, the server 106 (e.g., the processor 530) may obtain a plurality of users from the selected group. The server 106 may receive the obtained input through the communication module 510 of the server 106. By identifying group information corresponding to the obtained input, the processor 530 may identify the plurality of users. In an embodiment, in response to failing to receive the user group selection information, the processor 530 of the server 106 may repeatedly transmit a request for a group selection input to the user of the electronic device 101.

In operation 1807, the server 106 (e.g., the rival recommendation module 532) may recommend a rival among the plurality of users. That is, the rival recommendation module 532 of the server 106 may recommend the rival among the plurality of users according to a recommendation criterion selected by the user of the electronic device 101 or a recommendation criterion arbitrarily selected by the rival recommendation module 532 of the server 106. In an embodiment, the rival recommendation module 532 of the server 106 may recommend a rival list which includes all of the plurality of users having been obtained through the phone book group. In this case, the rival recommendation module 532 of the server 106 may transmit information about the users included in the rival list, to the communication module 440 of the electronic device 101 through the communication module 510 of the server 106.

Figure 19:
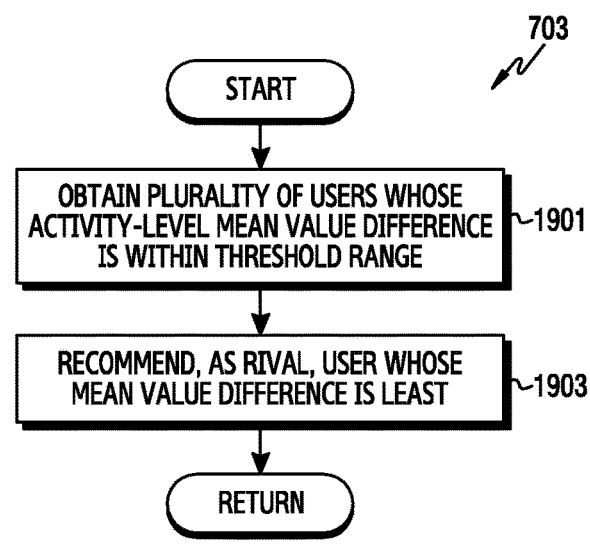
FIG. 19 illustrates a flowchart for recommending a rival having a similar activity level, based on first data, in a server according to various embodiments of the disclosure.

FIG. 19 illustrates a flowchart for recommending a rival having a similar activity level, based on first data, in a server according to various embodiments of the disclosure. FIG. 19 exemplifies an operation method of the server 106.

Referring to FIG. 19, in operation 1901, the server 106 (e.g., the processor 530) may obtain a plurality of users whose activity-level mean value differences are within a threshold range. The memory 520 of the server 106 may pre-store first activity information about the user of the electronic device 101 and information about the plurality of users. Accordingly, by comparing the first activity information about the user of the electronic device 101 and the information about the plurality of users, the processor 530 of the server 106 may identify the users whose activity-level mean value differences are within the threshold range. In an embodiment, in response to identifying that the user whose activity-level mean value difference is within the threshold range does not exist, the processor 530 of the server 106 may terminate the present algorithm, and recommend the rival according to another arbitrary recommendation criterion.

In operation 1903, the server 106 (e.g., the rival recommendation module 532) may recommend a user whose mean value difference is least, as the rival. In other words, the rival recommendation module 532 of the server 106 may recommend, as the rival, a user having an activity level most similar to that of the user of the electronic device 101. In an embodiment, the rival recommendation module 532 of the server 106 may perform recommendation on a basis of a consumed calorie, an exercise distance, an exercise time, etc., not the mean value.

Figure 20:
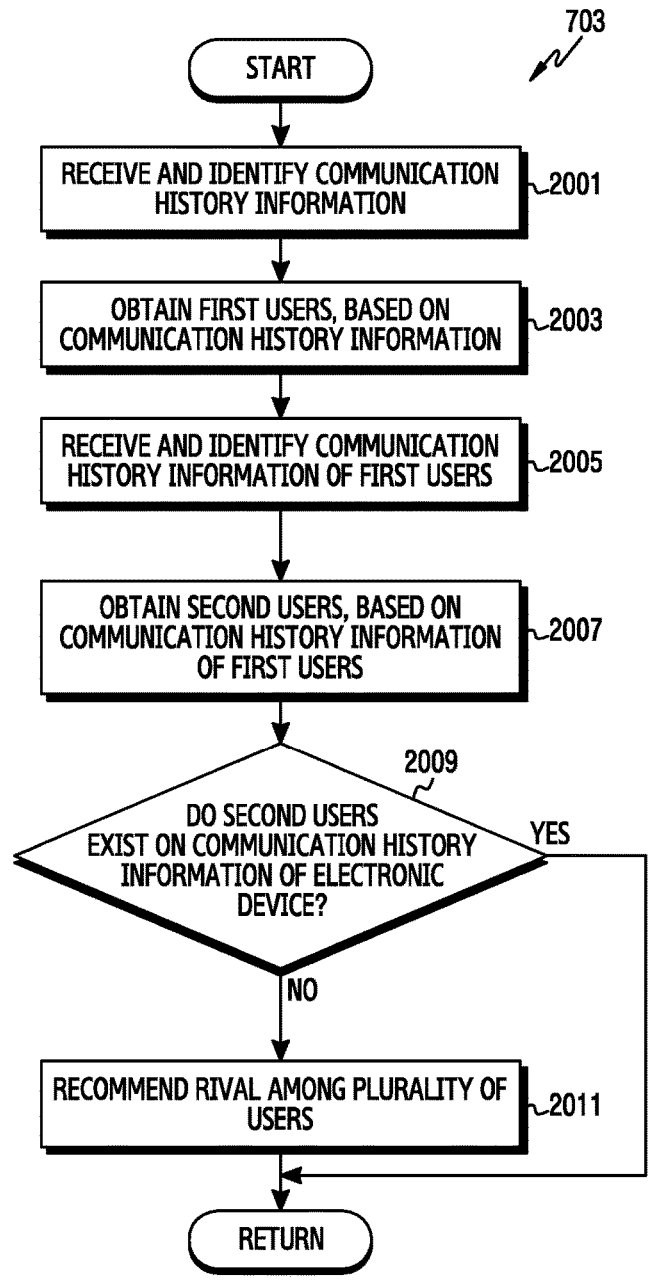
FIG. 20 illustrates a flowchart for recommending a rival, based on communication history information of users who have been obtained based on communication history information, in a server according to various embodiments of the disclosure.

FIG. 20 illustrates a flowchart for recommending a rival, based on communication history information of users who have been obtained based on the communication history information, in a server according to various embodiments of the disclosure. FIG. 20 exemplifies an operation method of the server 106.

Referring to FIG. 20, in operation 2001, the server 106 (e.g., the communication module 510 and the processor 530) may receive and identify communication history information. That is, the server 106 may receive and identify the communication history information in order to identify first users who will newly request for the communication history information through the communication module 510 of the server 106.

In operation 2003, the server 106 (e.g., the processor 530) may obtain the first users which are based on the communication history information. For example, the processor 530 of the server 106 may obtain the first users through the communication history information, and may newly transmit a communication history information request to the obtained first users. In an embodiment, in response to the request to the first users being rejected, the processor 530 of the server 106 may terminate the present algorithm, and may recommend a rival according to another recommendation criterion.

In operation 2005, the server 106 (e.g., the communication module 510 and the processor 530) may receive and identify communication history information of the obtained first users. In summary, the first users may be included in the communication history information of the electronic device 101. And, the communication history information received in operation 2005 is information received from the first users, and may be information for obtaining second users.

In operation 2007, the server 106 (e.g., the processor 530) may obtain second users which are based on the communication history information. For example, the second users may be acquired from the communication history information received from the first users who have been obtained through the communication history information of the electronic device 101. That is, the second users may be a plurality of users not included in the communication history information of the electronic device 101.

In operation 2009, the server 106 (e.g., the processor 530) may identify whether the second users exist on the communication history information of the electronic device 101. In response to information about the second users being included in the communication history information of the electronic device 101, the processor 530 of the server 106 may delete the corresponding users from the obtained plurality of users.

In operation 2011, the server 106 (e.g., the rival recommendation module 532) may recommend a rival among the plurality of users. Here, the plurality of users may be the remnant users excepting the users who exist on the communication history information of the electronic device 101 among the obtained second users. By deleting the overlapped users, the processor 530 of the server 106 may configure the plurality of users with only the second users not included in the first users. In an embodiment, the rival recommendation module 532 of the server 106 may transmit a rival list including all of the plurality of users, to the electronic device 101. In another embodiment, the rival recommendation module 532 of the server 106 may recommend, as a rival, one user among the rival list. In this case, the rival recommendation module 532 of the server 106 may recommend one user as the rival according to a recommendation criterion selected by the user of the electronic device 101 or a recommendation criterion selected by the rival recommendation module 532 of the server 106.

Figure 21:
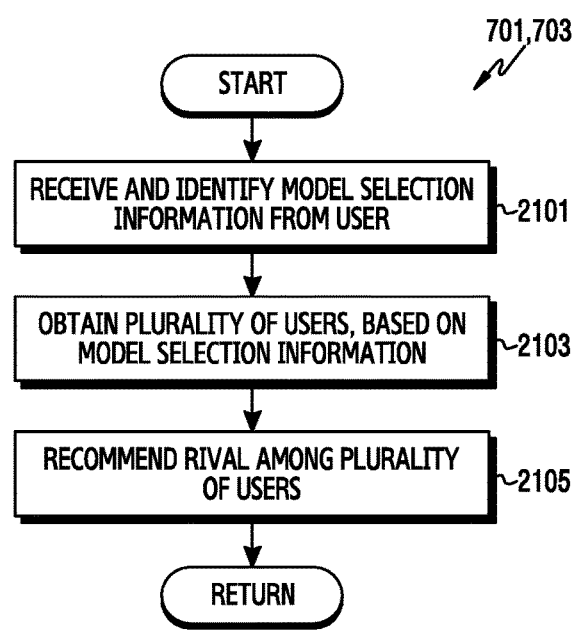
FIG. 21 illustrates a flowchart for recommending a rival, based on a specific model, in a server according to various embodiments of the disclosure.

FIG. 21 illustrates a flowchart for recommending a rival, based on a specific model, in a server according to various embodiments of the disclosure. FIG. 21 exemplifies an operation method of the server 106.

Referring to FIG. 21, in operation 2101, the server 106 (e.g., the communication module 510 and the processor 530) may receive model selection information from the user of the electronic device 101 and identify the received model selection information. Here, the model may be understood as being grouped according to a specific criterion. For example, the specific model may be grouped information of the same area, the same country, the same gender and the same age group. Also, the specific model, information about a virtual user, may be information about a virtual figure (e.g., a bot taking 8000 steps per day, etc.) or a celebrity (e.g., an entertainer). For example, the processor 530 may form a space for the specific model. That is, in response to the health care application 385 being executed, the electronic device 101 may receive space list information about the specific model through the communication module 440 of the electronic device 101. Accordingly, the processor 450 of the electronic device 101 may display a space list through the display 410, and may obtain a user input for specific model selection. Accordingly to this, the server 106 may receive the obtained information through the communication module 510 of the server 106.

In operation 2103, the server 106 (e.g., the processor 530) may obtain a plurality of users which are based on the model selection information. For example, in response to obtaining selection information about the same age group model, the processor 530 of the server 106 may obtain a plurality of users which belong to an age group of the user of the electronic device 101. In another example, in response to obtaining selection information about the same country model, the processor 530 of the server 106 may obtain a plurality of users who have the same country as a country registered by the user of the electronic device 101.

In operation 2105, the server 106 (e.g., the rival recommendation module 532) may recommend a rival among the plurality of users. The rival recommendation module 532 of the server 106 may recommend the rival among the plurality of users who have been obtained according to the model selection information. In this case, a recommendation criterion may be a recommendation criterion selected by the user of the electronic device 101 or a recommendation criterion arbitrarily selected by the rival recommendation module 532 of the server 106. In some embodiment, the rival recommendation module 532 of the server 106 may recommend only one user according to the selected recommendation criterion. For example, the one user may be a user having the most similar activity level among users of the same age group. In another embodiment, the rival recommendation module 532 of the server 106 may recommend a rival list which includes all of the plurality of users. In this case, information about the plurality of users who belong to the rival list may be transmitted to the communication module 440 of the electronic device 101.

Figure 22:
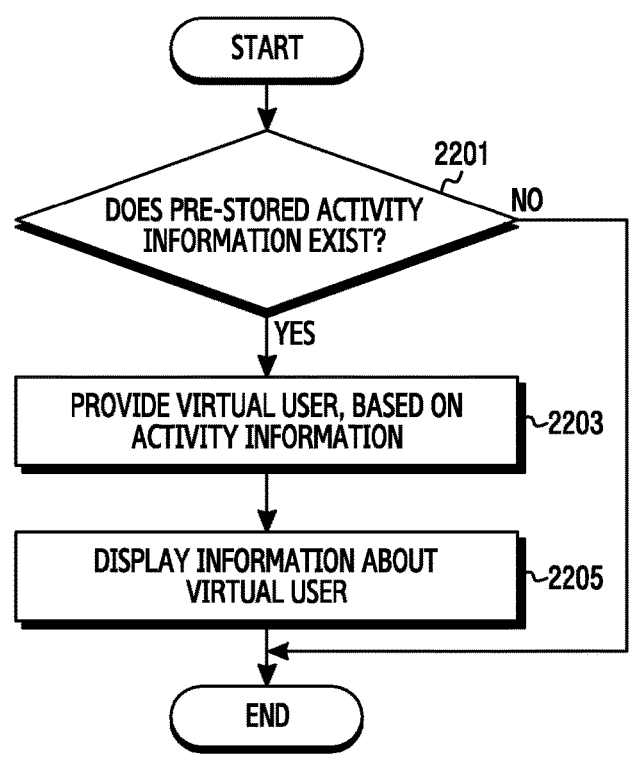
FIG. 22 illustrates a flowchart for providing a virtual user, based on first activity information, in an electronic device according to various embodiments of the disclosure.

FIG. 22 illustrates a flowchart for providing a virtual user, based on first activity information, in an electronic device according to various embodiments of the disclosure. FIG. 22 exemplifies an operation method of the electronic device 101.

Referring to FIG. 22, in operation 2201, the electronic device 101 (e.g., the processor 450) may identify whether pre-stored first activity information exists. For example, the processor 450 of the electronic device 101 may identify whether the first activity information exists, through a first activity information request to the memory 430. For example, in response to the pre-stored first activity information not existing, the processor 450 of the electronic device 101 may terminate the present algorithm, because information to provide the virtual user does not exist. On the other hand, in response to the pre-stored first activity information existing, the processor 450 of the electronic device 101 may perform the subsequent operations.

In operation 2203, the electronic device 101 (e.g., the processor 450) may provide a virtual user which is based on the first activity information. For example, the processor 450 of the electronic device 101 may request the first activity information to the memory 430 of the electronic device 101, and the memory 430 of the electronic device 101 may transmit the first activity information to the health care application 385. Accordingly, the processor 450 of the electronic device 101 may provide the virtual user, based on the first activity information. In this case, the user of the electronic device 101 may conduct challenge to the virtual user having his/her own past exercise record.

In operation 2205, the electronic device 101 (e.g., the display 410) may display information about the virtual user. The processor 450 of the electronic device 101 may provide the virtual user, and display the information about the virtual user through the display 410. For example, the display 410 of the electronic device 101 may display the information about the virtual user, and a UI (user interface) for giving invitation to the virtual user. Accordingly to this, the electronic device 101 may perform an operation, etc. of transmitting invitation to the virtual user and receiving a response from the virtual user.

Though not illustrated, the first activity information illustrated in FIG. 22 may be replaced with another activity information. Here, the another activity information may be second activity information about a past rival which has been pre-stored in the electronic device 101 through challenge that the electronic device 101 has conducted in the past. In this case, the user of the electronic device 101 may conduct challenge to the virtual user which is based on the past rival.

According to FIG. 4 to FIG. 22 explained above, the user of the electronic device 101 may receive a recommendation of a rival from the server 106. In various embodiments, the server 106 may recommend a rival or a rival list, and may transmit information about the rival or information about the rival list to the electronic device 101. In various embodiments, the server 106 may recommend the rival, based on a recommendation criterion. The recommendation criterion may include location information, place information, communication history information, activity information, etc. However, FIG. 4 to FIG. 22 illustrate only challenge making progress between individuals. Accordingly, FIG. 23A to FIG. 24B below illustrate challenge which may make progress in groups.

Figure 23A:
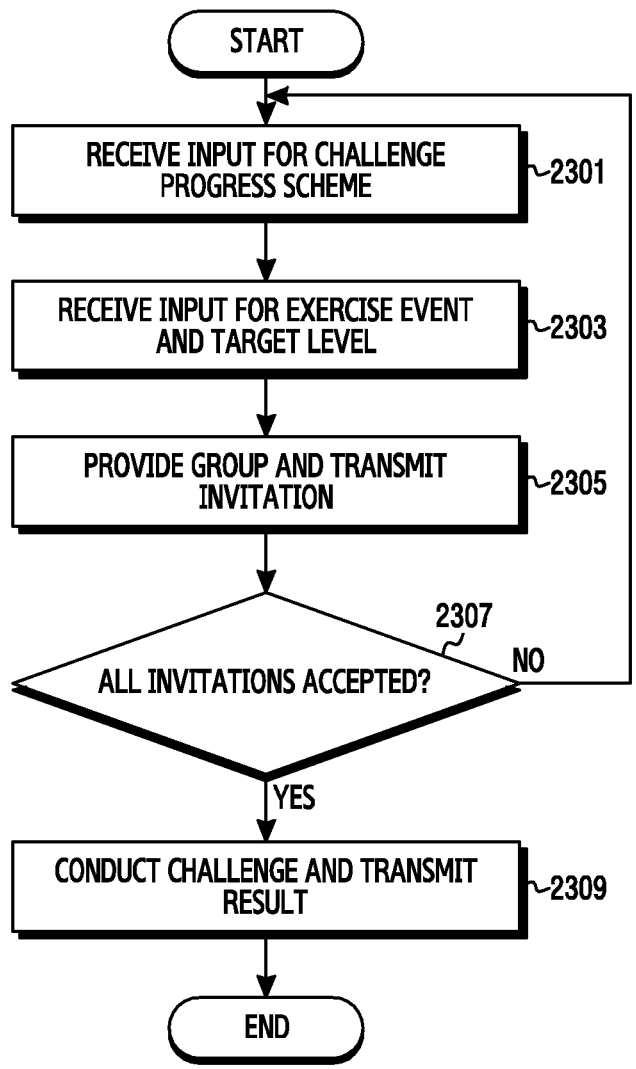
FIG. 23A illustrates a flowchart for conducting challenge, based on confrontation within a group according to various embodiments of the disclosure.

FIG. 23A illustrates a flowchart for conducting challenge, based on confrontation within a group, in a server according to various embodiments of the disclosure. FIG. 23A exemplifies an operation method of the server 106.

Figure 23B:
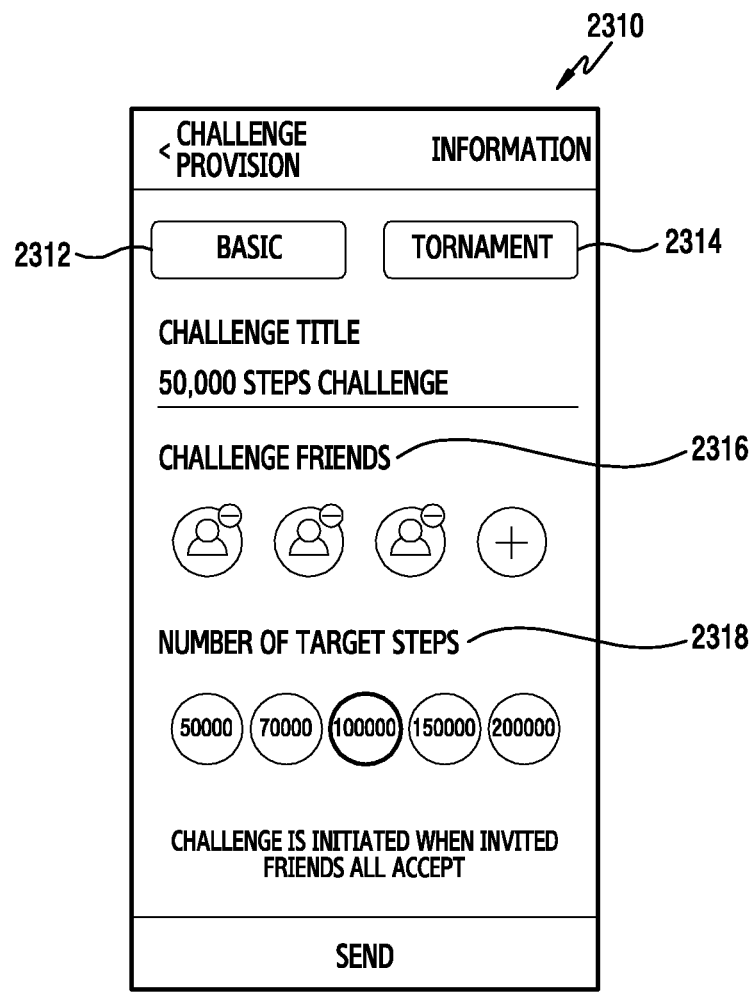
FIG. 23B illustrates a concrete example of screen display of a group provision UI (user interface) and a winner identification scheme at the time of confrontation within a group according to various embodiments of the disclosure.
Figure 23B:
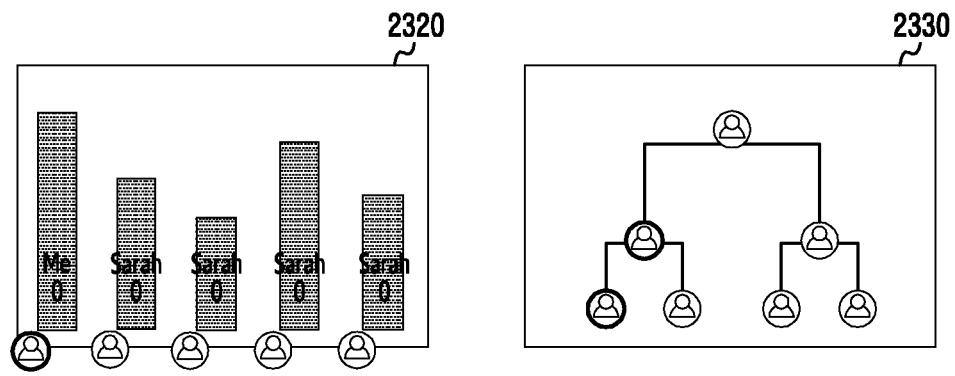

Referring to FIG. 23A, in operation 2301, the server 106 (e.g., the communication module 510) may receive an input for a challenge progress scheme from the electronic device 101. For this, the display 410 of the electronic device 101 may display a UI 2310 for group provision. Referring to FIG. 23B, the UI 2310 may include various input menus for challenge provision, and may obtain a user input for challenge provision. For example, the various input menus may include menus for challenge process schemes 2312 and 2314, member invitation 2316 and challenge information 2318. For example, the member invitation 2316 menu may display members forming a group. In some embodiment, the members forming the group may be a plurality of rivals arbitrarily recommended by the rival recommendation module 532 of the server 106, or may be comprised of users selected by the user of the electronic device 101. The challenge information 2318 may display information about challenge to be provided. Referring to FIG. 23B, the challenge information 2318 may display an exercise event (e.g., a walk event) and a target level (e.g., 10 thousand steps). The challenge progress scheme 2312 or 2314 may be, for example, one of a basic 2312 or a tournament 2314. In case of the basic 2312 progress scheme, the processor 530 of the server 106 may synthesize respective activity information of a plurality of users forming a group, to identify the ranking of each user. Also, a user who is close to the target level among the plurality of users may get a final victory. For example, as illustrated in FIG. 23B, numerical values of the activity information of the respective users may be displayed in the form of a bar graph 2320. Besides this, various methods such as a circle graph, etc. may be used. In case of the tournament 2314 progress scheme, the processor 530 may continuously conduct person-to-person confrontation between the plurality of users forming the group. For example, the person-to-person confrontation may make progress between a first member and a second member, and a third member and a fourth member. In response to members who have won a victory in the person-to-person confrontation becoming the first member and the fourth member, a member having got a victory of person-to-person confrontation between the first member and the fourth member may be a final winner.

In operation 2303, the server 106 (e.g., the communication module 510) may receive an input for an exercise event and target level from the user of the electronic device 101. For example, in response to the user of the electronic device 101 desiring to set a target level of 10 thousand steps in a walk event, the processor 450 of the electronic device 101 may obtain a user input for an exercise event and target level through the challenge information 2318 of FIG. 23B. The server 106 may receive the obtained input through the communication module 510 of the server 106, and the processor 530 of the server 106 may provide a space for challenge progress. Here, the space may be provided in private.

In operation 2305, the server 106 (e.g., the communication module 510) may transmit group provision and invitation. The server 106 may transmit an invitation message to electronic devices of users excepting the user of the electronic device 101, through the communication module 510 of the server 106. In this case, the user of the electronic device 101, a user who provides a group, may be denoted as a 'leader', a 'master', etc., and the remnant plurality of users may be denoted as a 'group element', a 'group member', etc. In response to the user of the electronic device 101 inputting a button 'send' on the UI 2310 of the electronic device 101, the server 106 may transmit an invitation message to communication modules of the electronic devices of the remnant users excepting the user of the electronic device 101, through the communication module 510 of the server 106.

In operation 2307, the server 106 (e.g., the communication module 510) may check whether all invitations have been accepted. That is, in response to the communication module 510 of the server 106 receiving acceptance messages from the remnant users excepting the user of the electronic device 101 within a group, the processor 530 of the server 106 may conduct challenge. On the other hand, in response to the communication module 510 of the server 106 receiving at least one rejection message from the remnant users excepting the user of the electronic device 101, the processor 530 of the server 106 may again perform operation 2301.

Figure 23C:
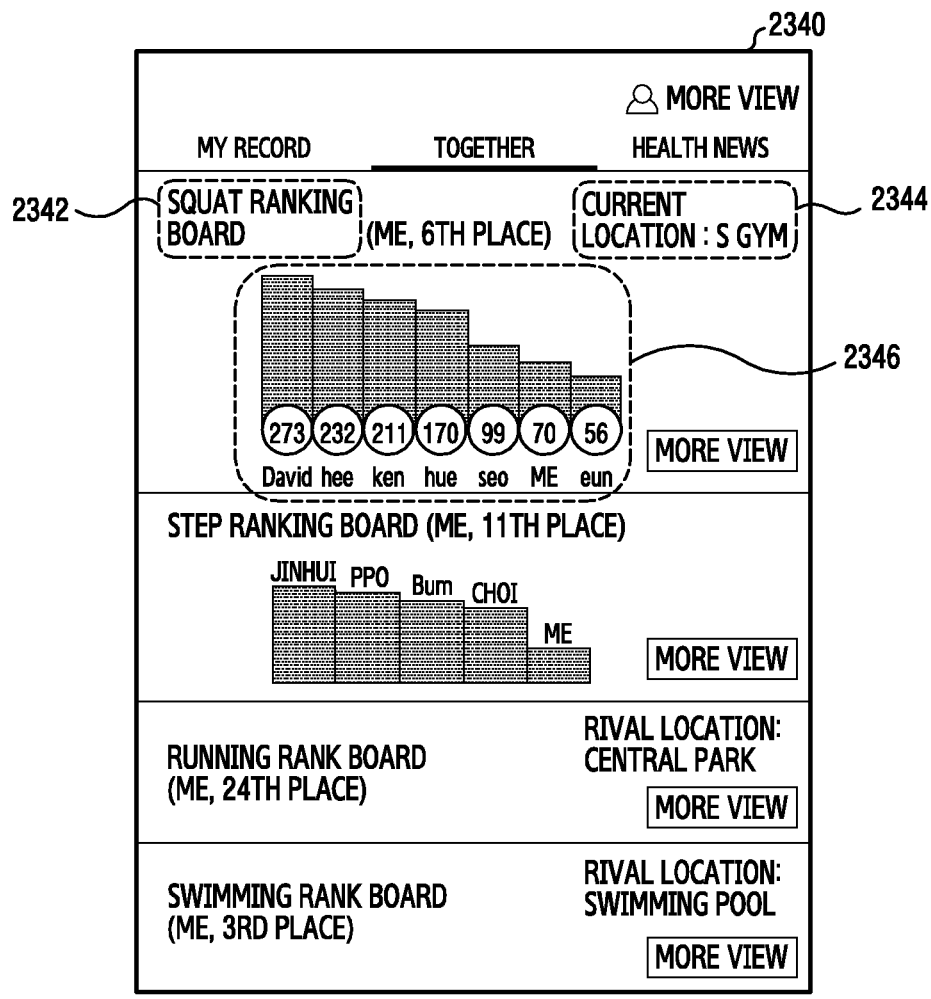
FIG. 23C illustrates a concrete example of screen display of a result being based on confrontation within a group according to various embodiments of the disclosure.

In operation 2309, the server 106 (e.g., the communication module 510) may transmit a challenge progress and result. That is, the server 106 may receive first activity information from electronic devices of all users within a group through the communication module 510 of the server 106, and may transmit a challenge result to the electronic devices. For example, the processor 530 of the server 106 may synthesize the received plurality of first activity information, to identify a winner of challenge within the group. For example, in case of the basic 2312 progress scheme, the server 106 may transmit activity information of all the users within the group, every predetermined cycle, to the electronic device of each user through the communication module 510 of the server 106, and a display of the server 106 may display the received activity information by the bar graph 2320. In another example, in case of the tournament 2314 progress scheme, the server 106 may transmit a victory and defeat result every person-to-person confrontation through the communication module 510 of the server 106. In response to a final victory being identified, the server 106 transmits the victory and defeat result to the electronic devices of all the users within the group, whereby the displays of the electronic devices may display the received victory and defeat result as the tournament result 2330. FIG. 23C illustrates a UI 2340 for a group challenge result displayed on the display 410 of the electronic device 101. Referring to FIG. 23C, the UI 2340 may display in the form of a bar graph 2346. However, in response to the user of the electronic device 101 conducting a plurality of group challenge, the display 410 of the electronic device 101 may divide and display each group challenge result. For example, a walk group challenge may be displayed, apart from a squat group challenge 2342. Accordingly, a squat group challenge 2342 result may be displayed through the bar graph 2346, and a walk group challenge result may be displayed through another bar graph provided in a separate space.

Figure 24A:
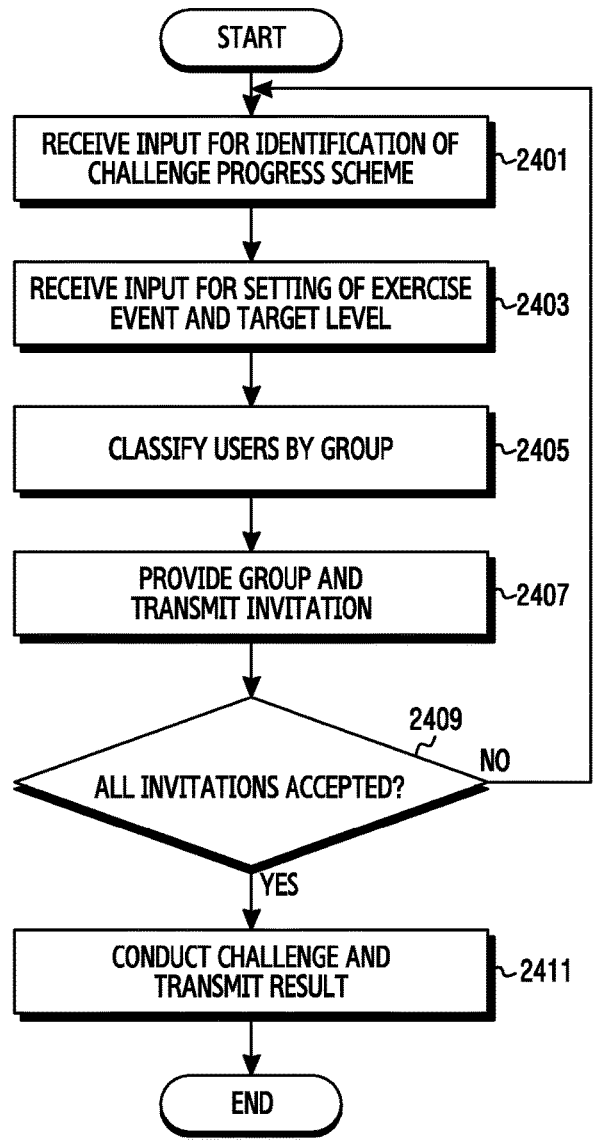
FIG. 24A illustrates a flowchart for conducting challenge, based on confrontation between groups according to various embodiments of the disclosure.

FIG. 24A illustrates a flowchart for conducting challenge, based on confrontation between groups, in a server according to various embodiments of the disclosure. FIG. 24A exemplifies an operation method of the server 106.

Figure 24B:
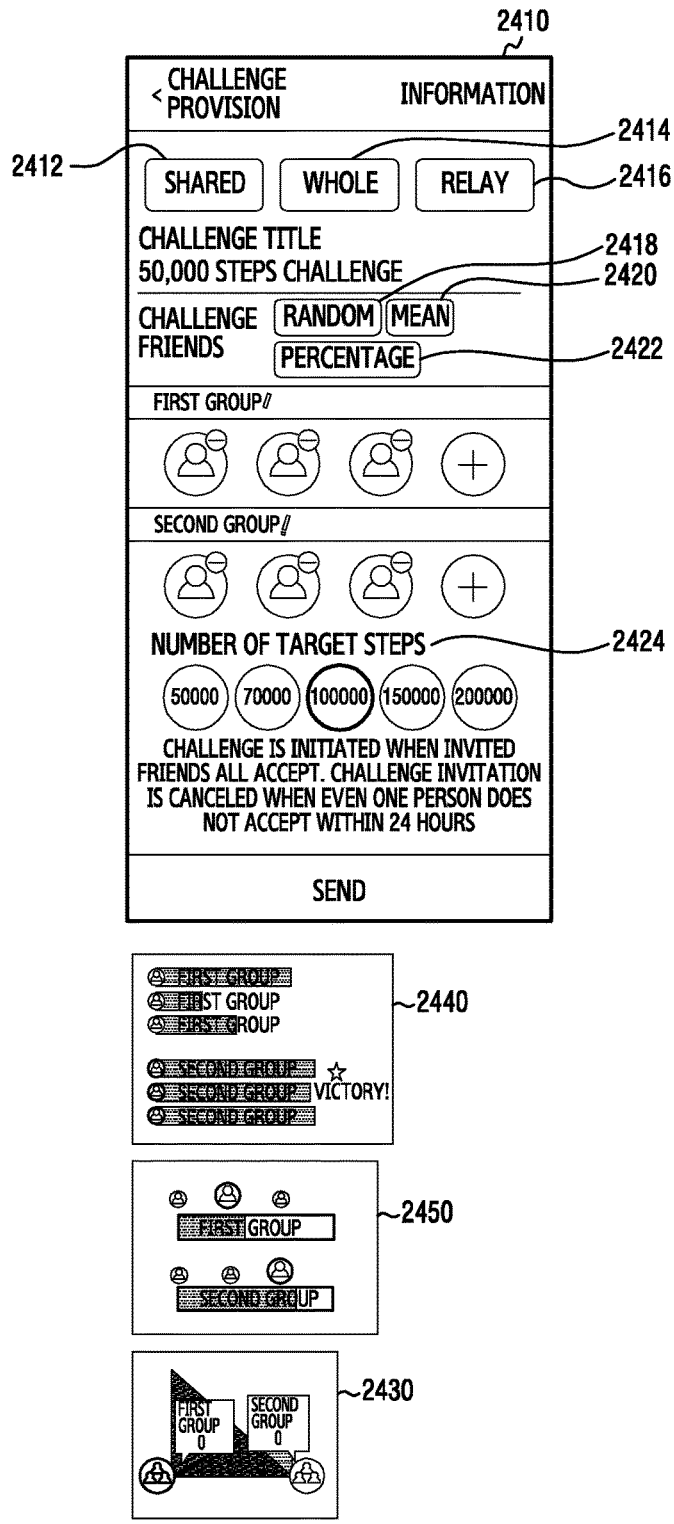
FIG. 24B illustrates a concrete example of screen display of a group provision UI and a victory group identification scheme at the time of confrontation between groups according to various embodiments of the disclosure.

Referring to FIG. 24A, in operation 2401, the server 106 (e.g., the communication module 510) may receive an input for a challenge progress scheme. A UI 2410 for group-to-group challenge provision may be displayed through the display 410 of the electronic device 101. Referring to FIG. 24B, the UI 2410 may include challenge progress schemes 2412, 2414 and 2416, group classification schemes 2418, 2420 and 2422, and challenge information 2424. The challenge information 2424 may include detailed information which is specified by a combination of event and target level information about group-to-group challenge to be provided. For example, the challenge information 2424 may display an event (e.g., a walk event) and a target level (e.g., 10 thousand steps). The challenge progress schemes 2412, 2414 and 2416 may be mainly divided into the shared 2412, whole 2414 and relay 2416 schemes.

In case of the shared 2412 progress scheme, the server 106 may receive respective first activity information from electronic devices of all users who participate in challenge through the communication module 510 of the server 106. The processor 530 of the server 106 may sum up numeral values on a per-group basis. A group having a high sum of the numerical values may win a victory. For example, when a numerical value summing up activity information of first group members is 90, and a numerical value summing up activity information of second group members is 95, a victory group may be a second group.

In case of the whole 2414 progress scheme, the server 106 may receive respective first activity information from electronic devices of all users who participate in challenge through the communication module 510 of the server 106. The processor 530 of the server 106 may identify a user who has achieved a target level every group. A group of which all the users forming the group have achieved the target level may win a victory. For example, in response to all the members of a first group achieving the target level, and one of members of a second group not achieving the target level, a victory group may be the first group.

In case of the relay 2416 progress scheme, the server 106 may receive first activity information from an electronic device corresponding to relay order in each group through the communication module 510 of the server 106. That is, each member may have unique relay order within a group. For example, when the first member of a first group fails to achieve a target level, and up to the second member of a second group achieve the target level, the second group may win a victory in response to the third member of the second group achieving the target level. The second member of the first group may not transmit activity information to the server 106, until before the first member of the first group achieves the target level.

In operation 2403, the server 106 (e.g., the communication module 510) may receive an input for setting of an exercise event and target level. For example, in response to the user of the electronic device 101 desiring to set a target level of 10 thousand steps in a walk event, the user of the electronic device 101 may input an exercise event and a target level through a challenge information 2424 menu.

The processor 450 of the electronic device 101 may obtain a user input, and may transmit information about the obtained input to the communication module 510 of the server 106 through the communication module 440 of the electronic device 101. The processor 530 of the server 106 may provide a space, based on the received user input. Here, the space may be provided in private.

In operation 2405, the server 106 (e.g., the processor 530) may classify users by group. For example, the group classification schemes 2418, 2420 and 2422 may be random 2418, mean 2420 or percentage 2422 schemes. In case of the random 2428 classification criterion, the processor 530 may randomly classify a plurality of users into a first group and a second group. In case of the mean 2420 classification criterion, the processor 530 may pair users whose activity-information mean values are similar to each other. Thereafter, the processor 530 may classify the paired users whose mean values are similar to each other into the first group and the second group, respectively. In case of the percentage 2422 classification criterion, the processor 530 may pair users having mutually similar percentages, based on percentage information. Thereafter, the processor 530 may classify the paired users having the similar percentages into the first group and the second group, respectively. Here, the communication module 510 of the server 106 may additionally receive information about a past percentage from each electronic device.

In operation 2407, the server 106 (e.g., the communication module 510) may transmit group provision and invitation. In this case, the user of the electronic device 101, a user who provides confrontation between groups, may be denoted as a 'leader', a 'master', etc., and the remnant plurality of users may be denoted as a 'group element' of each group, a 'group member', etc. For example, in response to the user of the electronic device 101 inputting a button 'send' on the UI 2410, the server 106 may transmit an invitation message to communication modules of electronic devices of the remnant users excepting the user of the electronic device 101 through the communication module 510 of the server 106.

In operation 2409, the server 106 (e.g., the communication module 510 and the processor 530) may check whether all invitation messages have been accepted. That is, in response to receiving acceptance messages from the remnant all users excepting the user of the electronic device 101 through the communication module 510 of the server 106, the processor 530 of the server 106 may conduct group-to-group challenge. Accordingly, in response to the server 106 receiving at least one rejection message from the remnant users excepting the user of the electronic device 101 through the communication module 510 of the server 106, the processor 530 of the server 106 may again perform operation 2401. On the other hand, in response to receiving acceptance messages from all the remnant users excepting the user of the electronic device 101 through the communication module 510 of the server 106, the processor 530 of the server 106 may conduct the group-to-group challenge.

In operation 2411, the server 106 (e.g., the communication module 510) may transmit a challenge progress and result. The processor 530 of the server 106 may identify a victory group of group-to-group challenge, based on the first activity information received from all the users. For example, in case of the shared 2412 progress scheme, the processor 530 of the server 106 may receive activity information from all users of a first group and a second group, and sum up the received activity information. In this case, the processor 530 of the server 106 may transmit a challenge result to all electronic devices of the users of the first group and the second group, and display the challenge result through the display 410 of the electronic device 101 as in a cumulative graph 2430. In another example, in case of the whole 2414 progress scheme, the processor 530 of the server 106 may identify a victory group by checking whether the respective users of the first group and the second group have achieved target levels, based on the activity information received from all the users. In this case, the processor 530 of the server 106 may transmit a challenge result to all electronic devices, and display the challenge result through the display 410 of the electronic device 101 as in a bar graph 2440. In a further example, in case of the relay 2416 progress scheme, the processor 530 of the server 106 may identify, as a victory group, a group whose all members first of all achieve a target level, based on activity information received from users corresponding to relay order in the first group and the second group. In this case, the processor 530 of the server 106 may transmit a challenge result to all electronic devices, and display the challenge result as in a relay graph 2450 through the display 410 of the electronic device 101.

Figure 25:
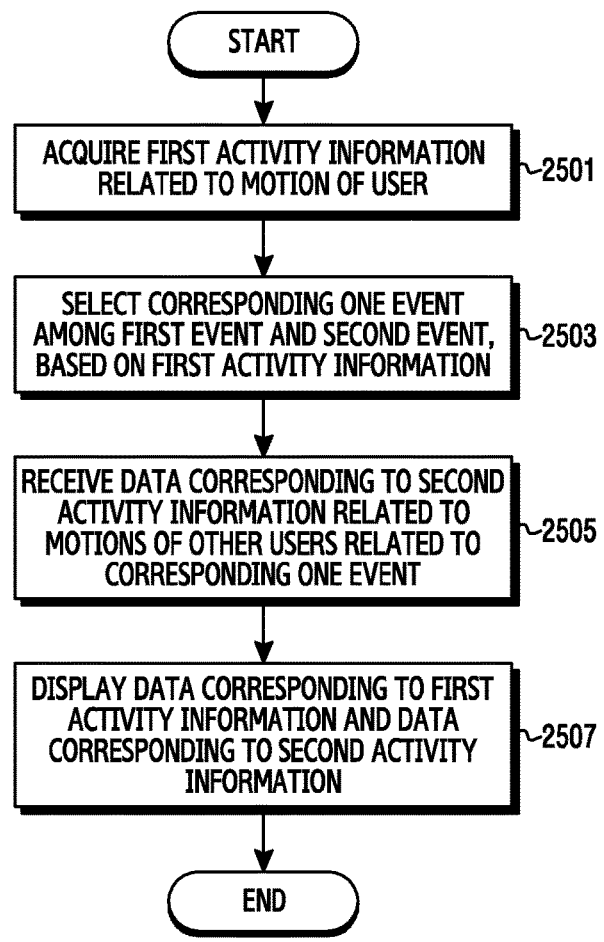
FIG. 25 illustrates a flowchart for conducting challenge in an electronic device according to various embodiments of the disclosure.

FIG. 25 illustrates a flowchart for conducting challenge in an electronic device according to various embodiments of the disclosure. FIG. 25 exemplifies an operation method of the electronic device 101.

Referring to FIG. 25, in operation 2501, the electronic device 101 (e.g., the processor 450) may acquire first activity information related to a motion of the user of the electronic device 101. For example, the sensor module 420 of the electronic device 101 may acquire sensor data which is based on the motion of the user of the electronic device 101. The processor 450 of the electronic device 101 may compare the acquired sensor data and a database of each exercise event, to acquire the exercise event and an exercise record. Accordingly, the processor 450 of the electronic device 101 may acquire the first activity information which includes information about the exercise event and exercise record.

In operation 2503, the electronic device 101 (e.g., the processor 450) may select corresponding one event among a first event and a second event, based on the first activity information. For example, the processor 450 of the electronic device 101 may select one event corresponding to the exercise event that is included in the first activity information. In another example, in response to the first activity information including information about several exercise events, the processor 450 of the electronic device 101 may display the exercise events through the display 410, and may receive a user input for the exercise event as well.

In operation 2505, the electronic device 101 (e.g., the communication module 440) may receive data corresponding to second activity information related to motions of other users which are related to the corresponding one event. Here, the second activity information may be distinguished from the first activity information of the user of the electronic device 101, and may include exercise event and exercise record information about other users.

In operation 2507, the electronic device 101 (e.g., the display 410) may display data corresponding to the first activity information and the data corresponding to the second activity information. The processor 450 of the electronic device 101 may identify the exercise event and exercise record information in the pre-stored first activity information about the user of the electronic device 101. Also, the processor 450 of the electronic device 101 may identify exercise event and exercise record information of other users, based on the received second activity information about the other users. Accordingly, the display 410 of the electronic device 101 may display the exercise records of the same event at the same time.

Figure 26:
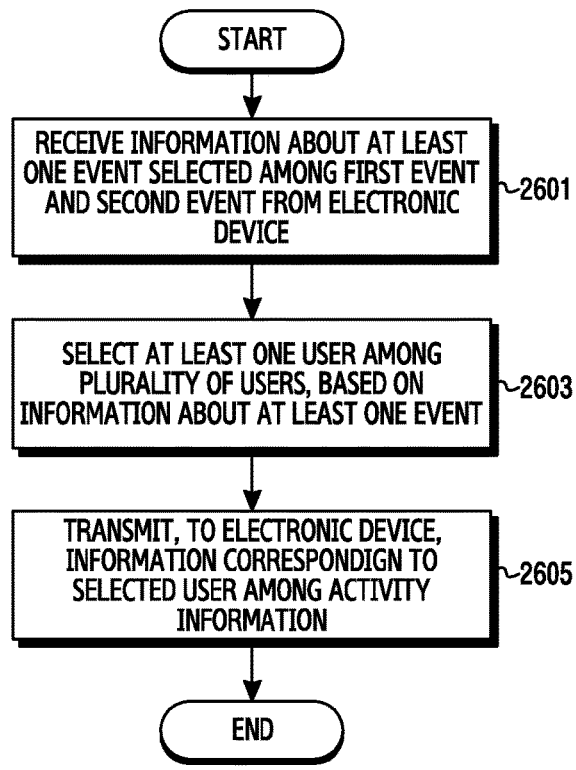
FIG. 26 illustrates a flowchart for conducting challenge in a server according to various embodiments of the disclosure.

FIG. 26 illustrates a flowchart for conducting challenge in a server according to various embodiments of the disclosure. FIG. 26 exemplifies an operation method of the server 106.

Referring to FIG. 26, in operation 2601, the server 106 (e.g., the communication module 510) may receive, from the electronic device 101, information about at least one event selected among a first event and a second event. The processor 450 of the electronic device 101 may obtain an input for a user selection of the first event and the second event. The communication module 440 of the electronic device 101 may transmit the obtained input to the communication module 510 of the server 106. Accordingly, the processor 530 of the server 106 may receive information about the event selection of the user of the electronic device 101 from the electronic device 101.

In operation 2603, the server 106 (e.g., the processor 530) may select at least one user among a plurality of users, based on the information about the at least one event. The processor 530 of the server 106 may receive the information about the event selection of the user of the electronic device 101, and may identify the plurality of users, based on the corresponding event. For example, in response to the user of the electronic device 101 selecting a walk event, the processor 530 of the server 106 may identify the plurality of users having selected the walk event, and select a rival among the corresponding plurality of users.

In operation 2605, the server 106 (e.g., the communication module 510) may transmit information corresponding to the selected user among the activity information, to the electronic device 101. For example, the processor 530 of the server 106 may pre-store, in the memory 520, information corresponding to the selected user. Here, the information corresponding to the selected user may be information about a concrete exercise record of an exercise event selected by the user of the electronic device 101. Accordingly, the processor 530 of the server 106 may transmit the information about the exercise record of the selected exercise event of the selected user, to the communication module 440 of the electronic device 101.

The term "module" used in the present document may include a unit consisting of hardware, software or firmware, and may be, for example, used interchangeably with the term "logic", "logic block", "component", "circuitry" or the like. The "module" may be an integrally configured component or the minimum unit performing one or more functions or a part thereof. The "module" may be implemented mechanically or electronically, and may, for example, include an ASIC (application-specific integrated circuit) chip, a FPGA (field-programmable gate array), or a programmable logic device, which has been known or will be developed in future, performing some operations. At least a part of an apparatus (e.g., modules or functions thereof) or method (e.g., operations) of various embodiments may be implemented as an instruction stored in a computer-readable storage medium in the form of a program module. In response to the instruction being executed by a processor (e.g., the processor 120), the processor may perform a function corresponding to the instruction. The computer-readable recording medium may include a hard disk, a floppy disk, a magnetic medium (e.g., a magnetic tape), an optical recording medium (e.g., a compact disk-read only memory (CD-ROM) and/or a digital versatile disk (DVD)), a magneto-optical medium (e.g., a floptical disk), an internal memory, etc. The instruction may include a code which is made by a compiler or a code which is executable by an interpreter. A module or program module of various embodiments may include at least one or more of the aforementioned constituent elements, or omit some constituent elements, or further include another constituent element. Operations carried out by a module, a program module or another constituent element of various embodiments may be executed in a sequential, parallel, repeated or heuristic manner, or at least some operations may be executed in a different order or may be omitted, or another operation may be added.

According to various embodiments of the disclosure, a non-transitory computer-readable recording medium which stores instructions for challenge progress may be provided. The instructions may be set such that, in response to the instructions being executed by the processor, the processor may perform sensing a user motion through at least one sensor, storing, in a memory, information about a first event and a second event related to an activity pattern of a user, acquiring first activity information related to the user motion by using the sensor, selecting a corresponding one event among the first event and the second event, based on the first activity information, receiving, from an external device, data corresponding to second activity information related to motions of one or more other users related to the corresponding one event by using the communication module, and displaying data corresponding to the first activity information and data corresponding to the second activity information by using a display operatively coupled with the processor.

According to various embodiments of the disclosure, the plurality of instructions may be set such that, before the receiving operation, the processor performs transmitting, to the external device, the data corresponding to the first activity information by using the communication module.

According to various embodiments of the disclosure, the plurality of instructions may be set such that, before the transmitting operation, the processor performs selecting the external device related to the corresponding one event, among one or more external devices being in a short distance from the electronic device.

According to various embodiments of the disclosure, the plurality of instructions may be set such that the processor performs acquiring location information of the electronic device by using the at least one sensor or communication module, and performing the selecting operation, based further on the location information.

According to various embodiments of the disclosure, the at least one sensor may include at least one of an acceleration sensor, a gyro sensor, a barometer, a geomagnetic sensor, a motion sensor and a GNSS (global navigation satellite system).

The embodiments of the present disclosure disclosed herein and shown in the drawings are merely specific examples presented in order to easily describe technical details of the present disclosure and to help the understanding of the present disclosure, and are not intended to limit the scope of the present disclosure.

Therefore, it should be construed that, in addition to the embodiments disclosed herein, all modifications and changes or modified and changed forms derived from the technical idea of the present disclosure fall within the scope of the present disclosure.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device comprising:
   a communication circuitry;
   at least one sensor;
   a memory; and
   at least one processor operatively coupled to the communication circuitry, the at least one sensor and the memory,
   wherein the at least one processor is configured to:
   identify, from a first user, a user input for generating an event regarding a first type of motion among multiple types of motions to be sensed by the at least one sensor;
   identify, in response to identifying the user input, one or more second users associated with the first type and distinct from the first user;
   display, in response to identifying the one or more second users, a user interface to the first user for requesting selection of one or more third users regarding the event, wherein the user interface displays the identified one or more second users with a representation indicating that the one or more second users may correspond to the one or more third users; and
   transmit, in response to the selection of the one or more third users by the first user, to one or more external electronic devices respectively corresponding to the selected one or more third users, one or more messages associated with the event.

2. The electronic device of claim 1, wherein the at least one processor is further configured to:
   identify, after transmitting the one or more messages, at least one third user among the one or more third users indicating acceptance of joining the event based on at least one message being received from at least one of the one or more external electronic devices; and
   adjust, in response to identifying the at least one third user, the user interface to request the user performing the first type of motion.

3. The electronic device of claim 2, wherein the at least one processor is further configured to:
   identify, based on the at least one sensor, first information regarding the first user performing the first type of motion in response to the adjusted user interface;
   identify, from the identified at least one third user, at least one second information has been detected from the identified at least one third user while performing the first type of motion; and
   display the identified first information and the at least one second information within the user interface.

4. The electronic device of claim 1, wherein the at least one processor is configured to:
   acquire location information of the electronic device by using the at least one sensor or communication circuitry; and
   perform the identification operation regarding the one or more second users, based further on the location information.

5. The electronic device of claim 3, wherein the at least one processor is configured to provide a result of comparing the first information and the at least one second information within the user interface.

6. The electronic device of claim 1, wherein the at least one processor is configured to:
   display, as the representation, one or more visual elements respectively corresponding to the identified one or more second users in the user interface,
   wherein the one or more visual elements respectively configured to make the corresponding second user to be inserted into or excluded from the one or more third users.

7. The electronic device of claim 1, wherein the at least one sensor comprises at least one of an acceleration sensor, a gyro sensor, a barometer, a geomagnetic sensor, a motion sensor, or a global navigation satellite system (GNSS).

8. The electronic device of claim 1, wherein the at least one processor is configured to:
   identify communication history information of the electronic device; and
   perform the identifying operation regarding the one or more second users, based further on the communication history information.

9. A non-transitory computer-readable recording medium comprising a plurality of instructions that, when executed by a processor of an electronic device, are configured to cause the electronic device to perform operations comprising:
   identifying, from a first user, a user input for generating an event regarding a first type of motion among multiple types of motions to be sensed by at least one sensor of the electronic device;
   identifying, in response to identifying of the user input, one or more second users associated with the first type and distinct from the first user;
   displaying, in response to identifying of the one or more second users, a user interface to the first user for requesting selection of one or more third users regarding the event, wherein the first user interface displays the identified one or more second users with a representation indicating that the one or more second users may correspond to the one or more third users; and
   transmitting, in response to the selection of the one or more third users by the first user, to one or more external electronic devices respectively corresponding to the selected one or more third users, one or more messages associated with the event.

10. The non-transitory computer-readable recording medium of claim 9, wherein the operations further comprises,
    identifying, after the transmitting of the one or more messages, at least one third user among the one or more third users indicating acceptance of joining the event based on at least one message being received from at least one of the one or more external electronic devices; and
    adjusting, in response to identifying the at least one third user, the user interface to request the user performing the first type of motion.

11. The non-transitory computer-readable recording medium of claim 10, wherein the operations further comprises,
    identifying, based on the at least one sensor, first information regarding the first user performing the first type of motion in response to the adjusted user interface;
    identifying, from the identified at least one third user, at least one second information has been detected from the identified at least one third user while performing the first type of motion; and
    displaying the identified first information and the at least one second information within the user interface.

12. The non-transitory computer-readable recording medium of claim 9, wherein the operations further method comprise:

acquiring location information of the electronic device by using the at least one sensor or communication circuitry; and performing the identifying operation regarding the one or more second users, based further on the location information.

13. The non-transitory computer-readable recording medium of claim 11, wherein the operations further comprise:

providing a result of comparing the first information and the at least one second information within the user interface.

14. The non-transitory computer-readable recording medium of claim 9, wherein the method operations further comprise:

identifying communication history information of the electronic device; and performing the identifying operation regarding the one or more second users based further on the communication history information.

\* \* \* \* \*